(12) United States Patent
Ferguson et al.

(10) Patent No.: US 12,003,344 B1
(45) Date of Patent: Jun. 4, 2024

(54) MANAGING LOCAL SENSOR DATA BASED ON PROFILE INFORMATION

(71) Applicants: William MacDonald Ferguson, Kelowna (CA); Jonathan Landers, Tampa, FL (US); Kenneth Deering, Bow, WA (US)

(72) Inventors: William MacDonald Ferguson, Kelowna (CA); Jonathan Landers, Tampa, FL (US); Kenneth Deering, Bow, WA (US)

( * ) Notice: Subject to any disclaimer, the term of this patent is extended or adjusted under 35 U.S.C. 154(b) by 0 days.

(21) Appl. No.: 18/087,520

(22) Filed: Dec. 22, 2022

(51) Int. Cl.
*H04L 12/28* (2006.01)

(52) U.S. Cl.
CPC ........ *H04L 12/2829* (2013.01); *H04L 12/282* (2013.01)

(58) Field of Classification Search
CPC .......................... H04L 12/2829; H04L 12/282
See application file for complete search history.

(56) References Cited

U.S. PATENT DOCUMENTS

| | | | | |
|---|---|---|---|---|
| 2014/0074257 | A1* | 3/2014 | Bhargava | H04L 12/282 700/47 |
| 2016/0132030 | A1* | 5/2016 | Marti | H04L 12/282 700/275 |
| 2016/0323393 | A1* | 11/2016 | Umphreys | G06Q 10/04 |
| 2017/0070842 | A1* | 3/2017 | Kulp | H04L 67/62 |
| 2017/0261951 | A1* | 9/2017 | Bandara | G06Q 50/06 |
| 2020/0081408 | A1* | 3/2020 | Wilberforce | H02J 13/00026 |
| 2022/0262517 | A1* | 8/2022 | Van Sickle | H02J 13/00001 |

* cited by examiner

*Primary Examiner* — Charles R Kasenge
(74) *Attorney, Agent, or Firm* — Knobbes Martens Olson & Bear LLP

(57) ABSTRACT

Aspects of the present disclosure correspond to managing premises by processing input data, such as the appliance's operational and usage profiles and/or individual's health and behavior profile. One aspect of the present disclosure related monitoring aspect based on processing the appliance's operational and usage profiles. For example, the appliance's operational parameters together with sensor data associated with the appliances can be utilized to monitor the premises. Another aspect of the present disclosure related to generating command instructions for the individual (e.g., premise user) based on the individual's health and behavior profile. For example, the usage of the appliances can provide to the individual one or more commanding instructions based on the individual's health and behavior profile.

28 Claims, 10 Drawing Sheets

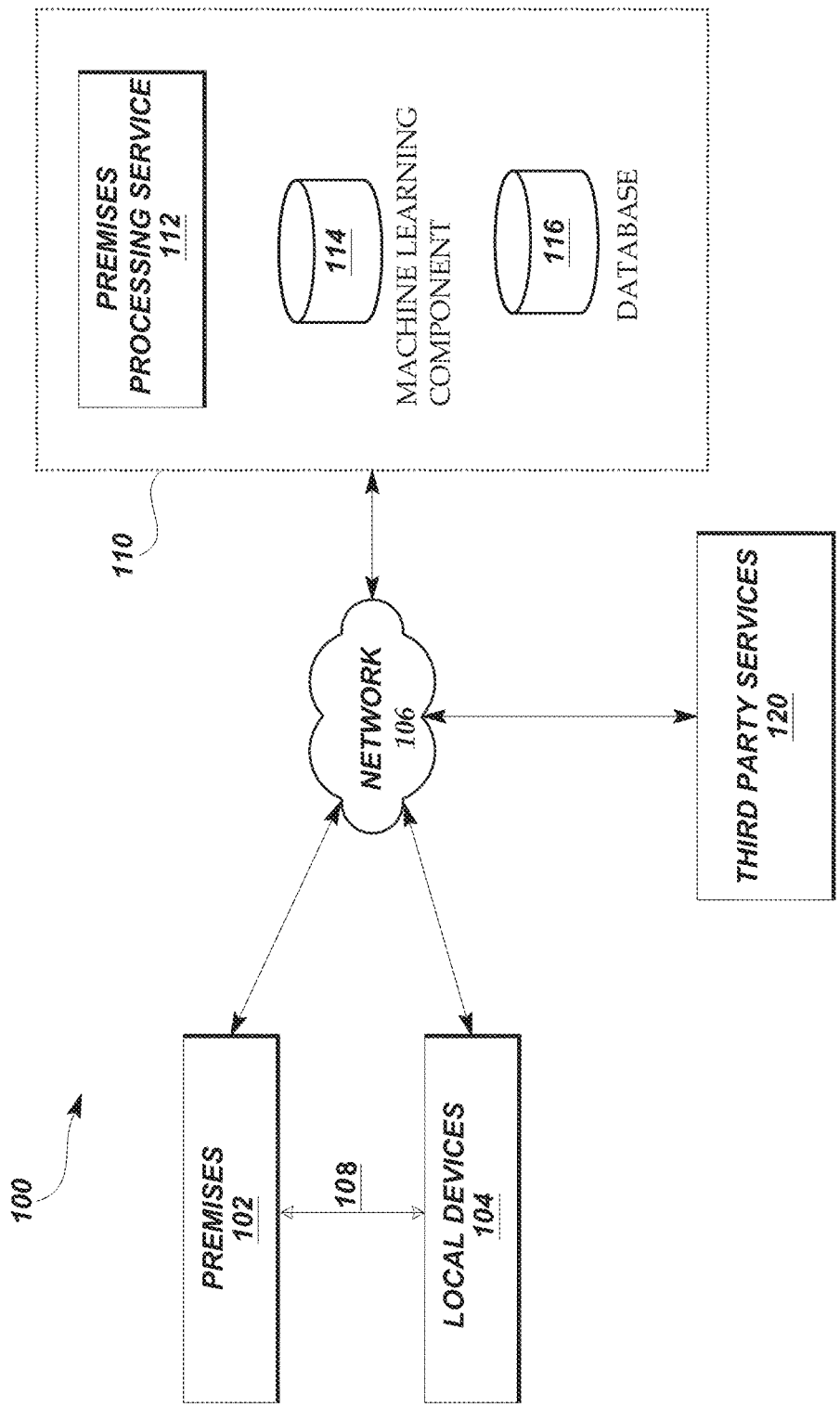

MANAGING LOCAL SENSOR DATA BASED ON PROFILE INFORMATION

BACKGROUND

Generally described, premises, such as homes, apartments, hotels, etc., may include a number of appliances. For example, a premise can include various heat generating applications, such as ovens, fryers, ranges, etc. Operation of such heat generating appliances in an unattended manner or negligent manner can lead to potential damage to the appliance and the premises. One attempt to mitigate or prevent damage caused by such unattended or negligent use of heat-generating appliances can include the integration of localized sensors to detect use and manual mitigation controls. For example, premises may be configured with a localized sensor to detect motion and a manual gas cutoff valve that removes the fuel source (e.g., natural gas) from a heat generating appliance in the event motion is not detected in proximity to an operational heat generating appliance within a threshold time. Such solutions are often considered "after-market" solutions that can be integrated in preinstalled heat generating appliances, such as by mounting the mitigation controls between the heat generating appliance and the power/fuel source.

As also generally described, computing devices and communication networks can be utilized to exchange data and/or information. In a common application, a computing device can request content from another computing device via the communication network. For example, a computing device can collect various data and utilize a software application to exchange content with a server computing device via the network (e.g., the Internet). Such software applications can include general communication applications for accessing the network, such as browser applications. Such general communication applications can access functionality provided by network-based services. The software applications can also include custom or specialized software applications configured to implement specific functionality alone or in combination with network-based services.

BRIEF DESCRIPTION OF THE DRAWINGS

This disclosure is described herein with reference to drawings of certain embodiments, which are intended to illustrate, but not to limit, the present disclosure. It is to be understood that the accompanying drawings, which are incorporated in and constitute a part of this specification, are for the purpose of illustrating concepts disclosed herein and may not be to scale.

FIG. 1A depicts a block diagram of a system that includes one or more premises, third party services, local devices, and a network service provider according to one embodiment;

DETAILED DESCRIPTION

Figure 1B:
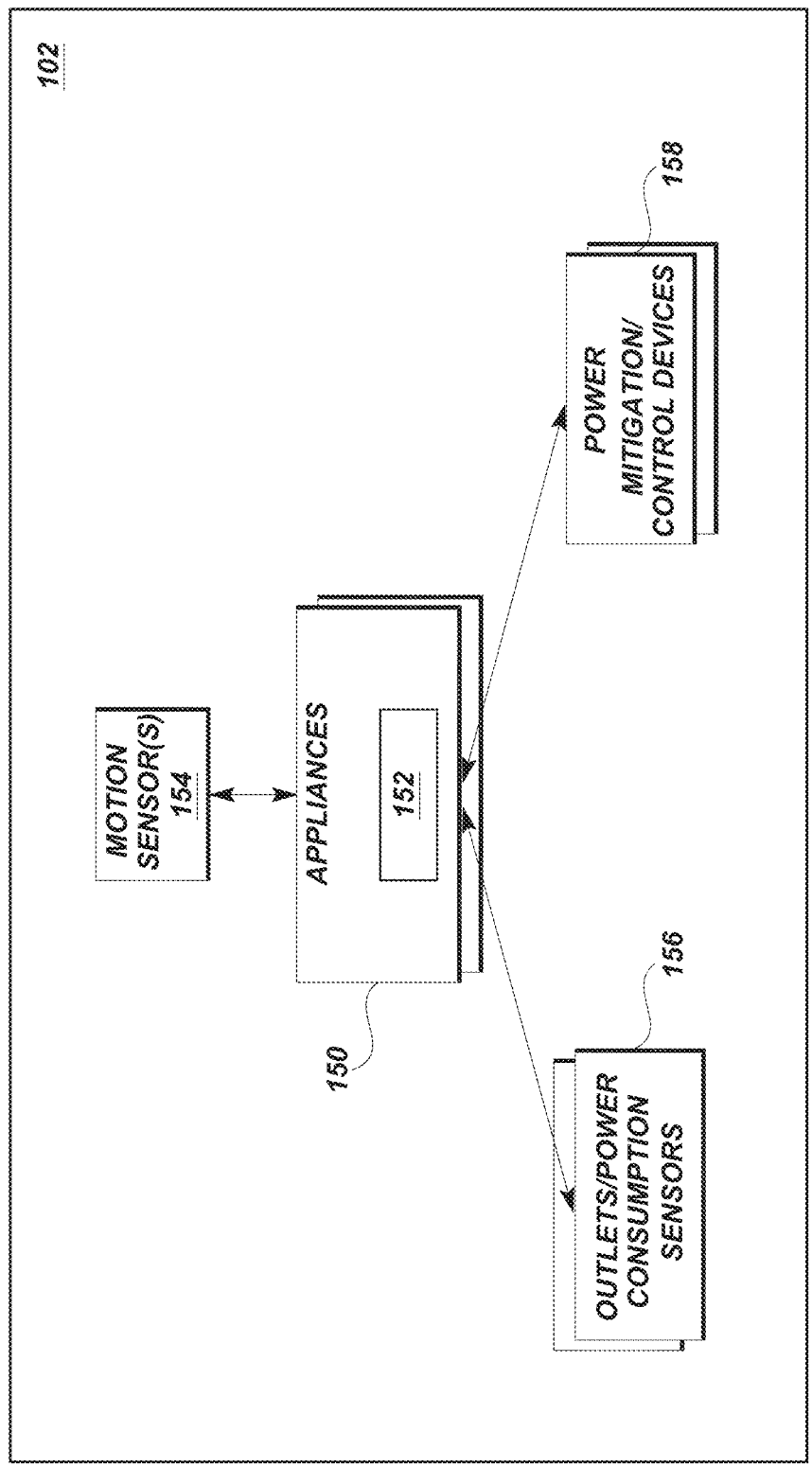
FIG. 1B depicts a block diagram of the premises according to one embodiment.

Aspects of the present application relate to systems and methods for managing appliances located in premises based on profile information. The profile information can include but is not limited to one or more appliance's operational profiles and usage profiles. Additionally, the profile information can also include one or more individual (e.g., user) health and behavior profiles. Illustratively, one or more aspects of the present application correspond to the utilization of premises management component(s) to obtain and/or process data generated from a plurality of sensors configured to generate data based on the type of sensor. The premises management component may be implemented in a manner to be local to premises and sensor data. The premises management component may also be implemented in a manner to be considered remote form the premises, such as via a network service. In other embodiments, multiple premises management components may work in conjunction, e.g., a combination of local and remote premises management components. For example, a premises management component can obtain sensor data from motion sensors, proximity sensors, power outlets, appliance use sensors, pressure sensors, temperature sensors, and the like. A grouping of individual sensor data of the plurality of sensors can be associated with at least one appliance within the premises. The present disclosure does not limit the types of appliances.

With reference to the above embodiments, the resulting grouped (and possibly processed) sensor data can be configured for further analysis either locally by the premises management component or via network services. Illustratively, one or more aspects of the present application correspond to the utilization of a local device. The local device can be one or more computing devices and configured to generate a local processing result based on processing the data received from the plurality of sensors, such as the premises processing component. Such local processing results can be processed by associating with the appliance's operational profile and usage profile and/or individual (e.g., user) health and behavior profiles. Based on the processing results, the local device can then generate one or more commands to the appliances, mitigation controls, output devices, etc. Additionally, the local device can generate notifications or requests for additional processing, such as to a network service.

Illustratively, one or more aspects of the present application correspond to the utilization of a network service, such as a premises processing service, to process data received from the plurality of sensors based on profile information. As described above, such profile information can include but is not limited to one or more appliance's operational profile and usage profile and/or individual (e.g., user) health and behavior profiles. Based on the processing results, the network service can then generate one or more command instructions to the individual premises components or directly to appliances. Additionally, the network service can generate notifications, data logging, requests for additional processing, such as to a local control component, and the like. Still further, in some embodiments, the network service and local device may work in cooperation, such as the distribution of processing tasks, allocation of authority/decision making, and the like.

In one aspect, one or more controllers associated with one or more appliances located on premises can perform the premises management based on input data. More specifically, the controllers may monitor the appliances' operation on the premises based on processing the input data. The input data can include processing results of a plurality of sensors associated with the appliances, the appliance's operational profile and usage profile, and/or individual (e.g., individual user or group of users) health and behavior profiles. Illustratively, one or more controllers located on the premises may receive data from appliances and a plurality of sensors associated with appliances. For example, the controllers receive the appliance's operational parameters in real time or near real time and store the operational parameters. Such operational parameters can be processed and stored as appliances' operational profiles.

In some embodiments, the appliance's operational profiles include the operational parameters by associating with data generated from sensors corresponding to the appliances. In some embodiments, the stored appliances' operational profile can further be processed and stored as the usage profile of the appliances. In these embodiments, if the individual controls the appliances, the controlled operational parameters of the appliances can be processed with generated sensor data corresponding to the appliances. For example, if an individual set the air conditioner temperature lower when the humidity of the premises is higher, the humidity data generated from the humidity measurement sensor associated with the lowering air conditioner (e.g., changing the operational parameter of the air conditioner) can be stored as a usage profile. These profiles can be stored in one or more storage mediums (e.g., internal and/or external storage mediums).

In some embodiments, the controllers further process the data received from a plurality of sensors based on the appliance's operational profile and the usage profile to monitor premises. For example, if a refrigerator's operational profile indicates that the door is opening for more than a threshold amount of time (e.g., 30 seconds), the controllers may process the refrigerator's usage profile to determine one or more processing results. In this example, if the usage profile indicates that the refrigerator's door is frequently opened for more than 30 seconds, it will not notify the individual. However, if the usage profile indicates that the door is not usually opened for more than 30 seconds, the controller may generate a processing result indicating that the refrigerator's door is opened with a recommendation to close the door.

In another aspect, the controller may generate one or more command instructions to individuals based on the individual's (e.g., user) profile, such as health and/or behavior profile. Such health and/or behavior profile can include but are not limited to one or more behavior or habit related to the individual's health. For example, the individual's profile can indicate that the individual needs to eat food at regular times, such as morning, afternoon, and dinner. In this example, the controller may monitor the appliances' operational and usage profiles to make a characterization, based on the collected sensor data, whether one or more individual(s) accesses appliances in a manner consistent with preparing food for cooking, actions associated with cooking food, eating food, etc. Such characterizations can be based on whether such activities are completed within established time windows consistent with individual habits/requirements or accepted group behaviors. For example, individual profiles may be generated with regard to food preparation/access in accordance with dietary requirements/habits such that controllers may process sensor data associated with a set of appliances based on the individual's profile (e.g., time of food access, type of food access, type of food preparation, type of food consumption, etc.). In another example, the individual's profile can be related to the individual's behavior not related to food consumption, such as saving electricity consumption from appliance use or tracking appliance use. The individual's health and/or behavior profile can be provided by the individual or automatically generated by utilizing one or more machine learned models. These controllers can generally be referred to as a premises management component. These are provided merely as examples, and the individual profile is not limited to these examples.

As described above, the premises processing service may perform one or more aspects of the premises management as described above. Illustratively, the premises processing service may receive the appliances' operational and usage profiles in real time or near real time to perform the monitoring aspect of the premises management. For example, the premises processing service may generate the processing results in real time or near real time by receiving and processing the input data, such as data generated from the plurality of sensors, the appliance's operational profile, and the usage profile. In one aspect, the premises processing service may provide processing results to one or more individuals or data repositories. Illustratively, the premises processing service may provide notifications or alarms based on the characterization of irregular activities on one or more appliances on the premises by monitoring the appliances' operational and usage profiles.

Still further, the premises processing service may provide instructions or commands that can be executed by one or more appliances (e.g., power outlets, ranges, stoves, microwaves, etc.) in accordance with the operational and usage profiles. The instructions or commands may correspond to commands or instructions transmitted via a network connection that can be processed by an appliance receiving the commands or instructions. Still further, in other embodiments, the instructions or commands may correspond to commands or instructions that may be received by intermediate devices that can cause physical manipulations associated with appliances, such as closing valves, turning appliance controls (e.g., dials), causing selection of breakers, and the like. In another aspect, the premises processing service may provide one or more notifications, alarms, instruction, commands to be executed by one or more appliances, etc., based on the individual's profile, such as health and behavior profiles, as described above. In some embodiments, the premises processing service may utilize machine learned model(s) to generate profiles and process the received inputs.

Generally, traditional premises management system for monitoring appliances located in the premises presents a limitation for individuals who use the appliances. More specifically, traditional premises management systems may only consider the current operational parameters of specific monitored appliances. In such a system, individuals can be notified when a specific event occurs, where the event is associated only with the current operational parameter of the appliances. Such an event is based on predefined rules, so the individual is notified whenever the event has occurred. In other implementations, traditional premises management systems may implement some form of mechanical control that attempts to mitigate the operation of an appliance based on limiting the supply of electrical power or some form of additional fuel source (e.g., natural gas), depending on the type of appliance. In other examples, a system may utilize some form of additional manual control that causes the modification of an operational control of an appliance, such as a mechanical mechanism that can rotate control knobs of a range or stove appliance or mechanically close a valve providing a fuel source to an appliance.

In one aspect, the traditional premises management system can also have a challenge in managing the premises associated with an individual's health and/or behavior. Illustratively, the system may only utilize the current operational parameter of the appliances to provide data that can be used in managing the appliances on the premises. In this regard, individual habits or actions are not considered in generating any type of processing results, such as logging data, providing notifications, generating control instructions, and the like. For example, if the individual's health regiment indicates that the individual needs to have a meal at regular times, the traditional premises management system does not incorporate any type of functionality that is configured to generate processing results based on the desired health regiment as the traditional premises management system is limited to monitoring for unattended appliance use.

To address at least a portion of the above-described deficiencies, one or more aspects of the present disclosure correspond to systems and methods for managing premises by utilizing data generated from a plurality of sensors and processing the data according to a set of one or more profiles. Illustratively, the set of profiles can include the appliance's operational profile and usage profiles related to the operation of individual appliances or groups of appliances. Additionally, the set of profiles can include one or more individual (e.g., profiles applicable to an identified user or group of users) health and behavior profiles. According to one or more embodiments as disclosed herein, one or more data processing result that indicates controlling at least one operational parameter of the appliance can be generated based on processing the appliance's operational profile and usage profile. Additionally, according to one or more embodiments as disclosed herein, one or more command instructions to use one or more appliances in the premises can be generated based on the appliance's operational profile and usage profile and individual (e.g., user) health and behavior profiles causing the generation and transmission of notifications, eliciting of actions, and the like.

Illustratively, a premises management component (local, remote, or combination) may monitor the operation of appliances located on the premises. In this illustration, the premises management component may process the data generated from a plurality of sensors and the operation of appliances. In some embodiments, each of the plurality of sensors can be associated with at least one appliance. Each of the plurality of sensors is not limited to a specific sensor, and it can be any sensor that can be associated with the appliance's functions, features, or any operational parameters. In some embodiments, the premises management component associates the sensor data with at least one operational parameter of the appliances. These operational parameters of the appliances can be generated in real time or near real time and may form an appliance operational profile. For example, if the appliance is an air conditioner, the premises management component may monitor the temperature of the premise that includes the air conditioner by using a temperature sensor located in the premise.

In some embodiments, the premises management component may monitor at least one operational parameter of appliances in the premises by processing data generated from the plurality of sensors, operational parameters of the appliances, usage of the appliance, and additional sensor data. Illustratively, information regarding the usage of the appliance may include various parameters, including time used, operational parameters during usage, or associated operational parameters (e.g., other applications that are used, etc.). In some embodiments, the usage of the appliance may provide an individual's previous usage of the appliance, which can be generally referred to as historical usage data. The historical usage data may include the same usage data as it was collected or can include subsets of the data, such as by filtering, removing duplicates, removing portions of usage data, and the like. For example, if an individual previously set the premise temperature differently based on time of day and outside temperature, the premises management component may monitor the air conditioner in the premise based on the previous usage of the appliance. This previous usage of the appliance can be included in the appliance's usage profile.

In some embodiments, the premises management component may generate one or more commanding instructions directed to the individual or a designate of the individual. In these embodiments, the commanding instruction may indicate recommendations to use the appliances, such as recommended usage of appliances, method of appliances' use, etc. For example, the commanding instruction may correspond to identifiable appliances (e.g., an indication of what appliance should be used), operational parameters of the identified appliances, and associated permissions and authentications. In some embodiments, the commanding instruction can be generated based on the processing of the data generated from one or more sensors from the plurality of sensors, the appliance's operational profile and usage profile, and/or individual (e.g., user) health and behavior profiles. The commanding instructions may be generated as application programming interface (API) instructions generated from templates defined in the various profiles. In other embodiments, the commanding instructions may be transmitted to additional controllers or processing components for translation into appropriate signals or commands.

Individual health and behavior profiles can be configured or otherwise provided by the individual, on behalf of an individual (e.g., a healthcare provider, guardian, supervisor, etc.), or can be provided from machine learned model configured to generate individual health and behavior profiles based on monitored sensor data. For example, if the individual's health profile indicates that the individual has a higher body max index (BMI) than the normal range, the premises management component may obtain data related to the individual's appliance operational profile during the mealtime, cooking appliance's usage, other sensor input (e.g., weight scale information), motion sensor data, and the like. In this example, if the data processing result indicates that the individual uses a microwave more than other cooking appliances, such as a stove and dishwasher, the commanding instruction may provide a warning to the individual to reduce consumption of instant food. The health and behavior profiles are not limited to the above examples, and the profile can be determined based on application. In some embodiments, the individual health profile can be provided by a user or authorized health provider/administrator. For example, if the individual has a critical health history related to a glucose, the individual's glucose level can be provided to the premises management component, and the premises management component provides a feedback or recommendation based on the received individual glucose level and usage of appliances. In some embodiments, the premises management component provides the monitoring result of the appliance's usage based on the individual health profile to third parties, such as the authorized health provider or administrator.

In some embodiments, the premises management component may track one or more operational parameters of at least one appliance. In these embodiments, data related to the tracking (or monitoring) operational parameter, such as the power consumption of the appliances, can be transmitted remotely to a user and/or third party services. For example, the power consumption of a premise that includes at least one appliance can be transmitted to an electrical power provider via a network in real time or near real time.

In some embodiments, a network service provider can provide various types of network-based services that are configurable to execute tasks based on inputs from the computing device. In some scenarios, it may be possible for an individual, such as customer or user, to manage appliances located on premises by utilizing the computing device. In certain scenarios, the network-based services can be configured to provide instructions to the individual to manage appliances located on the premises. In some embodiments, each individual network-based service can independently implement a premises processing service that corresponds to the individual's use of the service. In these embodiments, the service can include receiving data from appliances and various sensors and processing the data to generate one or more instructions based on the processing of the data, such as the appliances' operational and usage profiles, data received from various sensors, or the individual behavior or health profile. Accordingly, the network service can process the sensor data as described above for each individual premises management component. Still, further, the network service can process sensor data generated by multiple premises that are associated with some organizational criteria, such as apartment/condominium buildings, multiple premises associated with identified entities, and the like. In such embodiments, the profile information utilized by the premises management component can correspond to a collection of individual profiles, grouping of profiles (e.g., grouping of appliances or individuals), premises-based profiles, and the like.

In some embodiments, the premises processing service can perform one or more embodiments of the monitoring and generating command instructions, as described above. In some embodiments, the local device can also perform one or more of the monitoring and generating command instructions, as described above.

Although certain illustrative embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

FIG. 1A depicts a block diagram of an embodiment of the system 100. The system 100 can include a network 106, the network connecting a number of premises 102, local devices 104, and network-based services 112. Illustratively, the various aspects associated with the network service provider 110 can be implemented as one or more components that are associated with one or more functions or services. The components may correspond to software modules implemented or executed by one or more customer computing devices, which may be separate stand-alone local devices 104. Accordingly, the components of the network service provider 110 should be considered as a logical representation of the service, not requiring any specific implementation on one or more customer computing devices.

Network 106, as depicted in FIG. 1A, connects the devices and modules of the system. The network can connect any number of devices. In some embodiments, a network service provider provides network-based services to customer computing devices via a network 106. A network service provider 110 implements network-based services and refers to a large, shared pool of network-accessible computing resources (such as compute, storage, or networking resources, applications, or services), which may be virtualized or bare-metal. The network service provider 110 can provide on-demand network access to a shared pool of configurable computing resources that can be programmatically provisioned and released in response to customer commands. These resources can be dynamically provisioned and reconfigured to adjust to the variable load. The concept of "cloud computing" or "network-based computing" can thus be considered as both the applications delivered as services over the network and the hardware and software in the network service provider that provide those services.

In some embodiments, communication between the premises 102 and the network service provider 110 and between the local devices 104 and the network service provider 110 can occur via network 106, such as via one or more secured networks. For example, secure communications may occur via one or more local area networks that communicates securely via the Internet with the network service provider 110. The network 106 may include any wired network, wireless network, or combination thereof. For example, the network 106 may be a personal area network, local area network, wide area network, over-the-air broadcast network (e.g., for radio or television), cable network, satellite network, cellular telephone network, or combination thereof. As a further example, the network 106 may be a publicly accessible network of linked networks, possibly operated by various distinct parties, such as the Internet. In some embodiments, the network 106 may be a private or semi-private network, such as a corporate or university intranet. The network 106 may include one or more wireless networks, such as a Global System for Mobile Communications (GSM) network, a Code Division Multiple Access (CDMA) network, a Long Term Evolution (LTE) network, or any other type of wireless network. The network 106 can use protocols and components for communicating via the Internet or any of the other aforementioned types of networks. For example, the protocols used by the network 106 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein.

In some embodiments, the premises 102 and local devices 104 can be connected via a network 108. In these embodiments, network 108 comprises any combination of wired and/or wireless networks, such as one or more direct communication channels, local area network, wide area network, personal area network, and/or the Internet, for example. In some embodiments, the communication between the premises 102 and the local devices 104 may be performed via a short-range communication protocol, such as Bluetooth, Bluetooth low energy ("BLE"), and/or near field communications ("NFC").

In some embodiments, the networks 106, 108 may include some or all of the same communication protocols, services, hardware, etc. Thus, although the discussion herein may describe communication between the premises 102 and the local devices 104 via the network 108 and communication between the premises 102 and the network service provider 110, and between the local devices 104 and the network service provider 110 can occur via network 106, communications of the devices are not limited in this manner. The various communication protocols discussed herein are merely examples, and the present application is not limited thereto.

The premises 102 in FIG. 1A can connect to the networks 106, 108, and the network service provider 110. The premises 102 may be representative of a computing network associated with a plurality of controllers, such as the premises management component. In some embodiments, the premises management component can be configured to communicate with a plurality of sensors and one or more appliances via data communication buses.

In some embodiments, the premises 102 can be configured to include one or more individual physical building or enclosures, generally referred to as a premises, where each premise includes at least one appliance. The premises 102 can be configured to monitor these appliances according to one or more aspects as disclosed herein. Illustratively, the premises 102 may receive input data, such as current operating parameters of the appliances and data from a plurality of sensors associated with the appliances. The operating parameters of the appliances can be referred to as the appliance's operational profile. In this illustration, the premises 102 processes the received input data to monitor the premises, such that the premises 102 generate data processing result, indicating whether the individual or user might be required to change one or more operational parameters of at least one appliance. In some embodiments, the premises 102 can be configured to process individual appliance operational profiles or one or more appliance profiles corresponding to a plurality of appliances. The profile information may be provided as part of a configuration process and stored in memory.

Alternatively, the profile information may be provided based on local access to devices, such as mobile application, external memory devices, and the like. Data from a plurality of sensors can be applied or evaluated by selected operational profiles to generate processing results. For example, if an air conditioner is being operated in a premise and changes the temperature setting based on temperature sensors or other environmental inputs, the air conditioner's operational profile (e.g., mode of operation, temperature setting, etc.) can be mapped with sensor data, such as outside temperature, humidity, etc. The premises 102 processes data based on the mapping/associations of operational profiles with processed sensor data. The processing of appliance's operational profiles and usage profiles can be generated in real time or near real time and can be utilized in the monitoring aspect of the premises 102.

In some embodiments, the premises 102 can also be configured to generate one or more command instructions for the individual based on individual health and/or behavior profiles. For example, if the individual's health profile indicates that the individual has a higher body mass index than ordinary people and that the premise monitoring result indicates that the individual is using a microwave for the preparation of the meal, the premises 102 may provide a commanding instruction, such as reduce consumption of instant food. Such sensor data may be further combined with additional data, such as weight data from a weight measurement device (e.g., a weight scale) or blood glucose levels for processing according to operational profiles or behavioral profiles or that is accompanied with notification or other processing results as described herein.

In another example, if the individual has an allergy or medical condition that requires keeping the humidity of the premise in a certain level, the premises 102, based on the monitoring result of the humidifier's operational profile and usage profile, may provide a commanding instruction to change the humidifier's operational parameter. Such sensor data may be further combined with additional data, such thermostat data and temperature data for processing according to the operational profiles or behavioral profiles or that is accompanied by notifications or other processing results as described herein, In another example, if the individual's behavior profile indicates minimizing power consumption of the appliances in the premises 102, the premises 102 may generate a commanding instruction if the premises 102 detect any irregular power consumption from at least one appliance. These examples are provided merely as examples, and the individual's health and or behavior profile and commanding instructions are not limited to these examples.

Illustratively, the network service provider 110 can include a plurality of network-based services that can provide functionality responsive to data transmitted by the premises 102 and/or local devices 104, such as in the implementation of a set of microservices that are configured to provide underlying functionality to applications hosted by a service provider. As illustrated in FIG. 1A, the network service provider 110 can include a premises processing service 112. Illustratively, each service can be configured with defined functions that can be accessed based on communication or executable commands. The premises processing service 112 can be accessed directly with communications transited by premises 102 and local devices 104 via various interfaces. Additionally, the premises processing service 112 may also be considered dependent services or complimentary services that are accessed based on communications or commands from other services. Such dependent or complimentary services may or may not be directly accessible to communications from the premises 102 and local devices 104 (even if the execution of the dependent or complimentary services is being performed on behalf of the individual, such as a user). Without limitation premises processing service 112 can include virtualization services, streaming services, query processing services, data processing services, data storage or warehousing services, analytics services, database services, monitoring services, security services, content delivery services, and the like.

As depicted in FIG. 1A, the network service provider 110 can include the premises processing service 112. In some embodiments, the premises processing service 112 can be configured to manage premises according to one or more aspects as disclosed herein. Illustratively, the premises processing service 112 may receive input data, such as current operating parameters of the appliances and data from a plurality of sensors associated with the appliances in real time or near real time. The operating parameters of the appliances can be referred to as appliance's operational profile. In this illustration, the premises processing service 112 processes the received input data to monitor the premises, such that the premises processing service 112 generates data processing result(s), indicating whether the individual or user might be notified to change one or more operational parameters of at least one appliance. In some embodiments, the premises processing service 112 can be configured to process the appliance's operational profile and data from a plurality of sensors to generate a usage profile and recommendations. These appliances' operational profile and usage profiles can be generated in real time or near real time and can be utilized in the monitoring aspect of the premises processing service 112. In some embodiments, the premises 102 may access a database 116 in the network service provider 110 to acquire the usage profile.

In some embodiments, the premises processing service 112 can be configured to generate one or more command instructions for the individual based on profile information, such as individual health and/or behavior profile. For example, if the individual's health profile or received sensor data (e.g., weight scale data) indicates that the individual has a higher body mass index than a comparison group, health charts, etc. and that the premise monitoring result indicates that the individual is using a microwave for the preparation of the meal, the premises 102 may provide a commanding instruction, such as reduce consumption of food that has been characterized going against a prescribed treatment regime or defined action plan. In another example, if the individual has a medical condition, treatment plan, desired course of action, etc., that includes humidity setting of the premise at a certain level or range, the premises 102, based on the monitoring result of the humidifier's operational profile and usage profile, may provide a commanding instruction to change the humidifier's operational parameter. In another example, in a non-health related embodiment, if the individual's behavior profile indicates to minimize power consumption of the appliances in the premises 102, the premises 102 may generate a commanding instruction if the premises 102 detect any irregular power consumption from at least one appliance or to otherwise consider cumulative power attributes for a set of appliances for possible management. In this embodiment, the premises 102 can also roll up consumption for multiple distinct dwellings, such as an apartment complex. These examples are provided merely as examples, and the individual's health and or behavior profile and commanding instructions are not limited to these examples. In some embodiments, the individual health profile data can be provided by a user or health administrator. For example, if the individual has a critical health history related to glucose, the individual's glucose level can be provided to the premises management component, and the premises management component provides a feedback or recommendation based on the received individual glucose level and usage of appliances. In some embodiments, the premises management component provides the monitoring result of the appliances usage based on the individual health profile to third parties, such as the authorized health provider or administrator.

As depicted in FIG. 1A, the network service provider 110 can also include a machine learning component 114. In some embodiments, the machine learning component 114 provides the individual's health and behavior profiles based on bio data related to the individual. In other embodiments, the machine learning component 114 provides the individual's health and behavior profiles based on the individual's living pattern. In some embodiments, a number of different types of algorithms may be used by the machine learning component 126 to generate the models. For example, certain embodiments herein may use a logistical regression model, decision trees, random forests, convolutional neural networks, deep networks, or others. However, other models are possible, such as a linear regression model, a discrete choice model, or a generalized linear model. The machine learning algorithms can be configured to adaptively develop and update the models over time based on new input received by the machine learning component 126. For example, the models can be regenerated on a periodic basis as new human physical characteristics or bio information is available to help keep the predictions in the model more accurate as the information evolves over time. The machine learning component 126 is described in more detail herein.

Some non-limiting examples of machine learning algorithms that can be used to generate and update the parameter functions or prediction models can include supervised and non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, Apriori algorithms), artificial neural network algorithms (such as, for example, Perceptron), deep learning algorithms (such as, for example, Deep Boltzmann Machine), dimensionality reduction algorithms (such as, for example, Principal Component Analysis), ensemble algorithms (such as, for example, Stacked Generalization), and/or other machine learning algorithms.

These machine learning algorithms may include any type of machine learning algorithm, including hierarchical clustering algorithms and cluster analysis algorithms, such as a k-means algorithm. In some cases, the performing of the machine learning algorithms may include the use of an artificial neural network. By using machine-learning techniques, large amounts (such as terabytes or petabytes) of player interaction data may be analyzed to generate models.

As depicted in FIG. 1A, the network service provider 110 can also include a database 116 for maintaining information associated with any of the described functionality described herein. In some embodiments, the premises 102 may transmit appliance operational profile and data generated from a plurality of sensors in real time or near real time to the network service provider 110. These data, appliance operational profiles, and data generated by a plurality of sensors, can be stored in the database 116. In some embodiments, the usage profile is generated based on processing the appliance's operational profile, and data from a plurality of sensors can be stored in the database. In some embodiments, the premises 102 and local devices 104 request the usage profile, and usage profile is transmitted to the premises 102 and local devices 104.

As depicted in FIG. 1A, the system 100 can also include local devices 104. In some embodiments, the local device 104 may receive data processing results that indicates a request to control one or more appliances' operational parameters or commanding instruction as described above. In some embodiments, each local device can be configured to manage a single appliance, multiple appliances in a premise, and/or multiple appliances in all of the premises. For example, the local device can be a computing device and includes a user interface that can display appliances in each premise. An individual or user of the local device may utilize the user interface to select one or more appliances or premises to operational parameters of one or more appliances based on data processing results, such as monitoring and command instructions generated one or more aspects as disclosed in the above.

In some embodiments, the local devices 104 can be configured to perform the monitoring and generating command instruction aspects, as disclosed in the present disclosure. In some embodiments, the local device 104 may receive data from the plurality of sensors associated with one or more appliances and generate the appliances' operational profile and usage profile to perform the monitoring aspect as described above. In some embodiments, the local device may perform one or more aspects of generating the command instructions as described in the above.

The system 100 can further include one or more third party services 120 that can include any one of a number of services/entities that may be configured to either provide inputs to the network service provider 110 or receive processing results based on process data, such as appliance's operational profile, usage profile, data generated from the plurality of sensors, and individual's health and behavior profiles. By way of illustrative example, the third-party services 120 can provide one or more data/information that can be utilized to process the data, such as the individual's health or behavior information, the premises' geographic information, power consumption information, etc. The one or more third party services 120 can also include service providers that can provide additional information that may be utilized in the premises monitoring and commanding instruction generation processes. The third-party services 120 further include entities that can utilize processing results, such as a third party authorized to manage the premises, security providers, landlord/location management authorities, etc.

FIG. 1B depicts a block diagram of an embodiment of the premises 102. Each of the premises 102 can include one or more appliances and a plurality of sensors, such as motion sensor 154, and/or outlet/power consumption sensors 156. Details of the operation of one or more components in FIG. 1B, such as motion sensors 154 associated with one or more appliances 152 are described in U.S. Pat. No. 10,241,530, filed Apr. 13, 2017, titled "CONTROLLING HEAT CAPABILITY OF APPLIANCE ACCORDING TO USER PROXIMITY AND NOTIFYING REMOTE USERS VIA INTERNET FOR INCREASED SAFETY," which is incorporated by reference its entirety herein. In addition, the appliance 152, as disclosed in the present disclosure, is not limited to a specific appliance, and it can include any general appliance.

The outlet/power consumption sensors 156, as described in FIG. 1B, can be utilized to measure power consumption from a single appliance or multiple appliances 152. In some embodiments, the power consumption measured by the outlet/power consumption sensors 156 can be utilized as the appliance's profile and/or usage profile. The power mitigation/control devices 158 can be connected with one or more appliances 152 and configured to control the power supply to the appliances based on input received from an individual. In some embodiments, the individual may provide the input by using the local device 104 via the network 106 or 108.

Figure 1C:
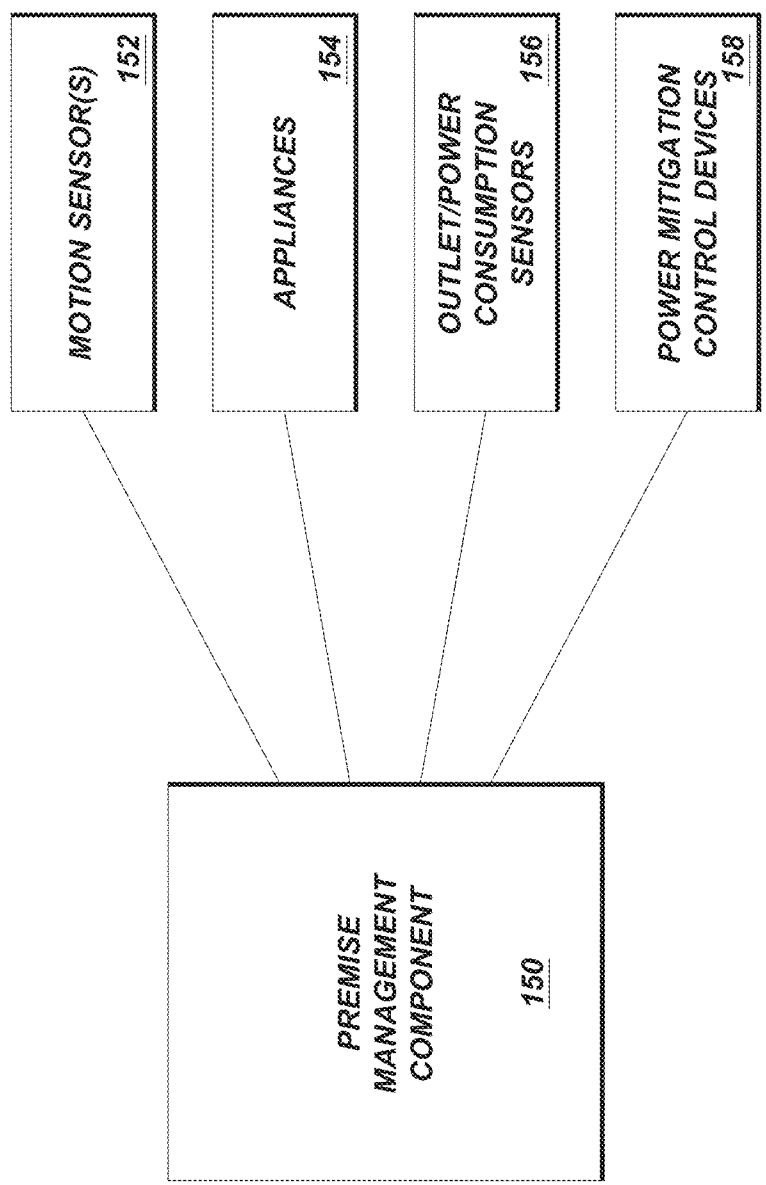
FIG. 1C depicts a block diagram of the premises management component according to one embodiment.

In some embodiments, as shown in FIG. 1C, the premise management component 150 can be configured to transmit/receive data from the appliances 152, motion sensor 154, outlet/power consumption sensors 156, and power mitigation/control devices 158. In some embodiments, the premise management component 150 can include internal data storage, wireless data transfer circuitry, data communication bus, one or more processor (e.g., microprocessor), GPS signal receiver, etc. In these embodiments, the premise management component 150 may be connected to one or more appliances 152 and configured to process data to perform one or more aspects as disclosed herein.

In alternative embodiments, the premise management component 150 can be implemented to the appliances 152. The implementation of the premise management component 150 is not limited to the present disclosure. Furthermore, while FIGS. 1B and 1C include particular sensors, such as motion sensor 154 and outlets/power consumption sensors 156, the present disclosure does not limit the type and/or the number of sensors. For example, the premises 102 can include, by way of non-limiting examples, some or all of the following sensors: one or more motion detection sensors; one or more processors, such as a microcontroller; one or more barometers; one or more location devices (e.g., GPS signal receiver) and/or transmitter sensors; one or more gyroscope sensor configured to provide an orientation of the dashcam with an accurate precision; one or more light sensor configured to automatically adjust display lights based on the ambient light; one or more barometer configured to measure the atmospheric pressure; one or more user (or driver) identification sensors, such as a fingerprint sensor and iris scanner; one or more digital compass configured to provide an orientation information of the appliances; one or more infrared sensors; one or more pressure sensors; one or more temperature sensors; one or more air humidity sensors; one or more Near Field Communication (NFC) sensors; one or more human gesture recognition sensor configured to recognize one or more person's gesture; one or more position sensors' one or more vibration sensors; one or more force sensors; one or more piezo sensors; one or more strain gauges; one or more liquid flow level sensors; and one or more photo optics sensors. Illustratively, the sensors directly provide sensing data for processing directly by one or more operational profiles or behavioral profiles. In some embodiments, the sensors may be accompanied by additional control or processing systems that may allow for the processing of the sensor data. For example, a control system may be able to process sensor data to remove erroneous data or duplicative data, normalize data, and the like. In another example, a control system may be able to provide additional processing of sensor or device data to form additional sensor data. Illustratively, measurement of radio signal data, such as NFC or Wi-Fi signals typically used for communications networks, can be processed to detect the presence and movement of physical items (e.g., humans) based on detected changes in received or transmitted radio signals.

Still, further, the sensors can include can also include additional devices or equipment that may provide some data for use in the processing of other sensor data or otherwise provided as context with processed sensor data. Such additional device or equipment can include illustratively include data from a number of categories or types of devices, including, but not limited to, medical equipment (e.g., blood pressure measurement data, blood glucose measurement data, pulse oximetry measurement data, etc.), fitness equipment (e.g., exercise tracking data, heartrate measurement data, etc.), health and wellness equipment (e.g., weight sensor data, temperature measurement data, sleep tracking measurement data, etc.), and the like. In some embodiments, the data from the additional devices and equipment can be combined or otherwise processed in conjunction with the sensor data and processed according to one or more profiles as described herein.

Figure 2A:
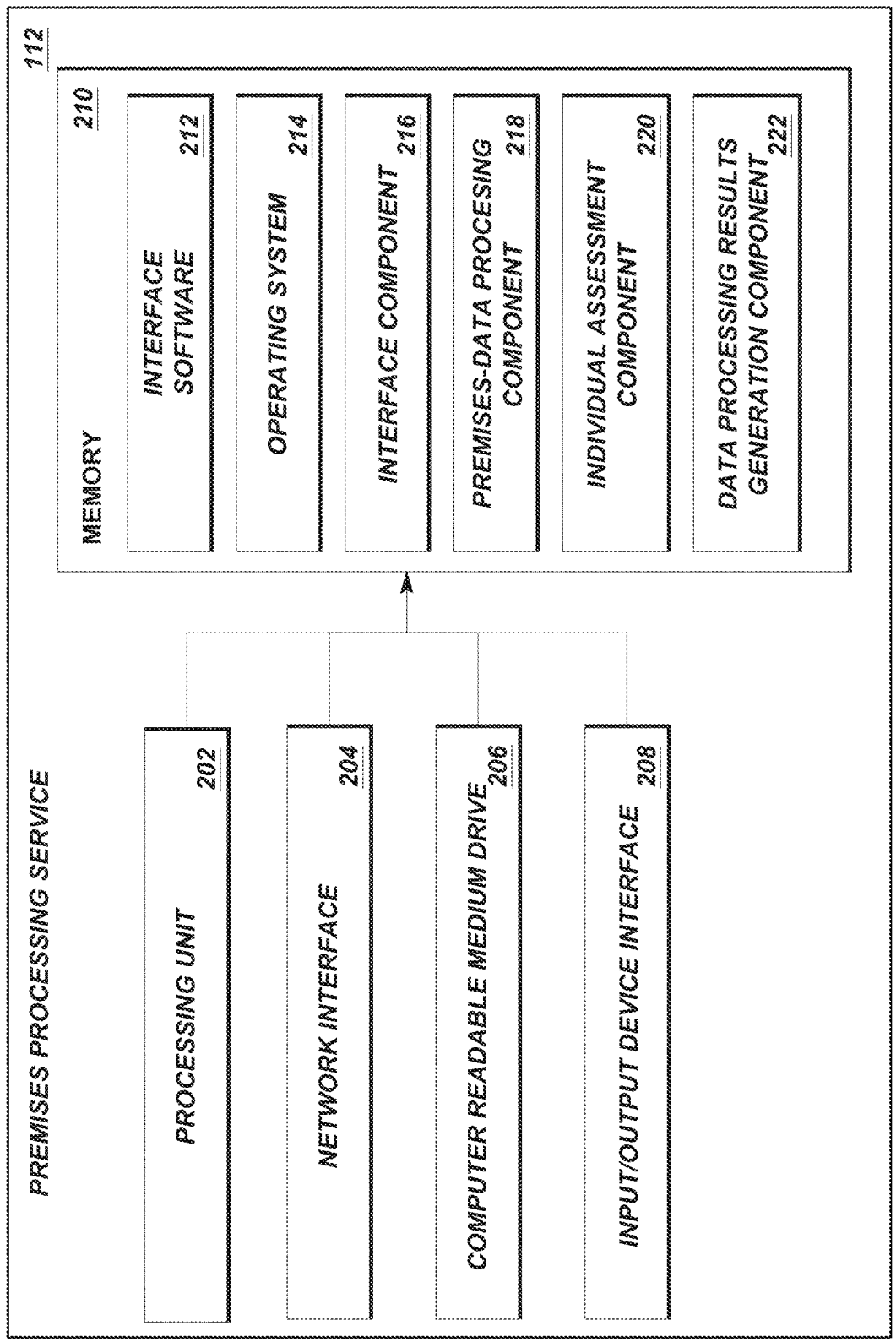
FIG. 2A is a block diagram of illustrative components of a premises processing service according to one or more embodiments.

FIG. 2A depicts one embodiment of an architecture of an illustrative premises processing service 112. The premises processing service 112 can be configured to monitor the premises based on processing data received from the premises 102 and/or local devices 104. The premises processing service 112 can also be configured to generate command instructions based on processing data received from the premises 102 and local devices according to one or more operational profiles or health and behavior profiles received from local device 104, the third party services 120, and/or machine learning component 114. In some embodiments, the premises processing service 112 can apply an appliance's operational profile based on data received from the premises. For example, the premises 102 transmit the current operational parameters of the appliances, and the operational parameters can be processed locally according to the appliance's operational profile. In some embodiments, the premises processing service 112 categorizes the appliance's operational profile based on each appliance. In other embodiments, the premises processing service 112 group the appliances based on each appliance located in each premise. In some embodiments, the appliance's operational profile can be processed with data received from a plurality of sensors, where each sensor can be associated with one or more appliances. For example, if the appliance is a humidifier, and a humidity measurement sensor and temperature sensor's output data can be associated with the humidifier's operational parameter. In this example, if the individual changes the humidifier's settings differently, the different settings will be processed with the humidity and temperature sensors' output data, such that the individual changes the humidifier's settings according to the humidity and/or temperature of the premise that include the humidifier. This data of the appliance's operational parameter associated with the individual's usage or data generated from the plurality of sensors can be referred to as an appliance usage profile, which can include individual usage data, cumulative usage data, grouped usage data, and the like. This usage profile can be stored in the database 116. In some embodiments, the usage profile can be stored for each individual or group of individuals, such as a family.

The general architecture of the premises processing service 112 depicted in FIG. 2A includes an arrangement of computer hardware and software components that may be used to implement aspects of the present disclosure. As illustrated, the premises processing service 112 includes a processing unit 202, a network interface 204, a computer-readable medium drive 206, and an input/output device interface 208, all of which may communicate with one another by way of a communication bus. The components of the premises processing service 112 may be physical hardware components or implemented in a virtualized environment.

The network interface 204 may provide connectivity to one or more networks or computing systems, such as the network 106 of FIG. 1. The processing unit 202 may thus receive information and instructions from other computing systems or services via a network. The processing unit 202 may also communicate to and from memory 210 and further provide output information for an optional display via the input/output device interface 208. In some embodiments, the premises processing service 112 may include more (or fewer) components than those shown in FIG. 2A.

The memory 210 may include computer program instructions that the processing unit 202 executes in order to implement one or more embodiments. The memory 210 generally includes RAM, ROM, or other persistent or non-transitory memory. The memory 210 may store an operating system 214 that provides computer program instructions for use by the processing unit 202 in the general administration and operation of the premises processing service 112. The memory 210 may further include computer program instructions and other information for implementing aspects of the present disclosure. For example, in one embodiment, the memory 210 includes interface software 212 for communicating with other components or services and performing one or more aspects as disclosed herein.

The memory 210 may include an interface component 216 for receiving sensor data generated from the plurality of sensors. In some embodiments, each sensor can be associated with one or more appliances. In some embodiments, the plurality of sensors may transmit the data to the premises processing service via the interface component 216. In these embodiments, the interface component 216 may support a variety of data formats. For example, each of the plurality of sensors may transmit the data in different data formats, and the interface component 216 can be configured to receive or process these different formats. For example, the interface component 216 may convert or parse each of the data received from the plurality of sensors to one or more data formats that can be further used in the premises processing service 112. In some embodiments, the interface component receives data from one or more appliances, such as the current operational parameters of the appliance. In these embodiments, each parameter from the operational parameters can have different data format based on type of operational parameters or types of appliances. For example, if the appliance is an air conditioner, the data generated from the air conditioner's temperature parameter and power module can have a different data format. In this example, the interface component 216 may convert these appliance operational parameters to one or more data formats utilized in the premises processing service 112. In some embodiments, the interface component 216 also receives data from the third-party services 120 or the local devices 104, and the received data can be converted into one or more data formats utilized in the premises processing service 112.

The memory 210 may also include a premises-data processing component 218 configured to process data received from premises 102, local devices 104, and/or third-party services 120. In some embodiments, the premises-data processing component 218 may generate processed data related to the current appliances' operational parameters by associating with the sensor data, and these data can be referred to as the appliance's operational profile. In these embodiments, the premises-data processing component 218 may categorize each appliance's operational profile based on premises, type of appliances, feature of the appliances, etc. In some embodiments, the premises-data processing component 218 categorizes (e.g., map) each of the sensor output data based on the appliances corresponding to each sensor. For example, data received from a temperature sensor in a premise can be associated with specific appliances, such as an air conditioner, stove, and humidifier. In these embodiments, the appliance's operational profile associated with one or more data received from the sensors can be stored in the database 116 as the usage profile.

In some embodiments, the premises-data processing component 218 may identify an individual's health and behavior profiles. For example, the premises-data processing component 218 may identify the individual's health and behavior profiles from output data generated from the machine learning component 114. For example, a plurality of individuals may be associated with an individual profile or set of profiles based on health and behavior profiles generated from the machine learning component 114. In another example, each individual may provide their profile, or partial profile, manually, and the profiles are stored in the database. In some embodiments, the premises-data processing component 218 group the individuals based on one or more common premises where the individuals use or reside. For example, a family may use a common premise, and the premises-data processing component 218 may group the individuals in the family.

The memory 210 may also include an individual assessment component 220 for assessing individual or individuals. In some embodiments, the individual assessment component 220 may include one or more appliance usage models based on individual health and behavior profiles. For example, an appliance(s) usage model may be associated with the individual's body mass index and may indicate that the individual is required to reduce the usage of the microwave during the meal preparation time or that the individual may limit the use of cooking related appliances to certain numbers per day. In this example, the individual assessment component 220 may perform the assessment of the individual's usage (e.g., daily usage of the appliances) based on the models, such that if the individual uses microwaves instead of a stove during a set time window (e.g., defined meal time) or that the individual is using the cooking appliances more than a defined number of times, the individual assessment component 220 may provide notifications to the individual or other designated representatives. Still further, the behavioral profile may further cause the generation of log files/journal files for tracking or other historical data. In another example, if the individual's behavior indicates that the individual has behavior to save the energy consumption of appliances, the individual assessment component 220 may access the operational parameters of the appliances based on motion detection sensors, such that if the air conditioner is set too low temperature, while the detection sensors do not detect the human movement in the premise, the individual assessment component 220 may notify to the individual about the power consumption.

The memory 210 may also include data processing results generation component 222 for providing data processing results. In some embodiments, based on data generated from the premise processing component 218, the data processing results generation component 222 may perform premises monitoring. In these embodiments, based on the data processing results, the data processing results generation component 222 may automatically adjust the appliance's operational parameters or notify the individual.

Figure 2B:
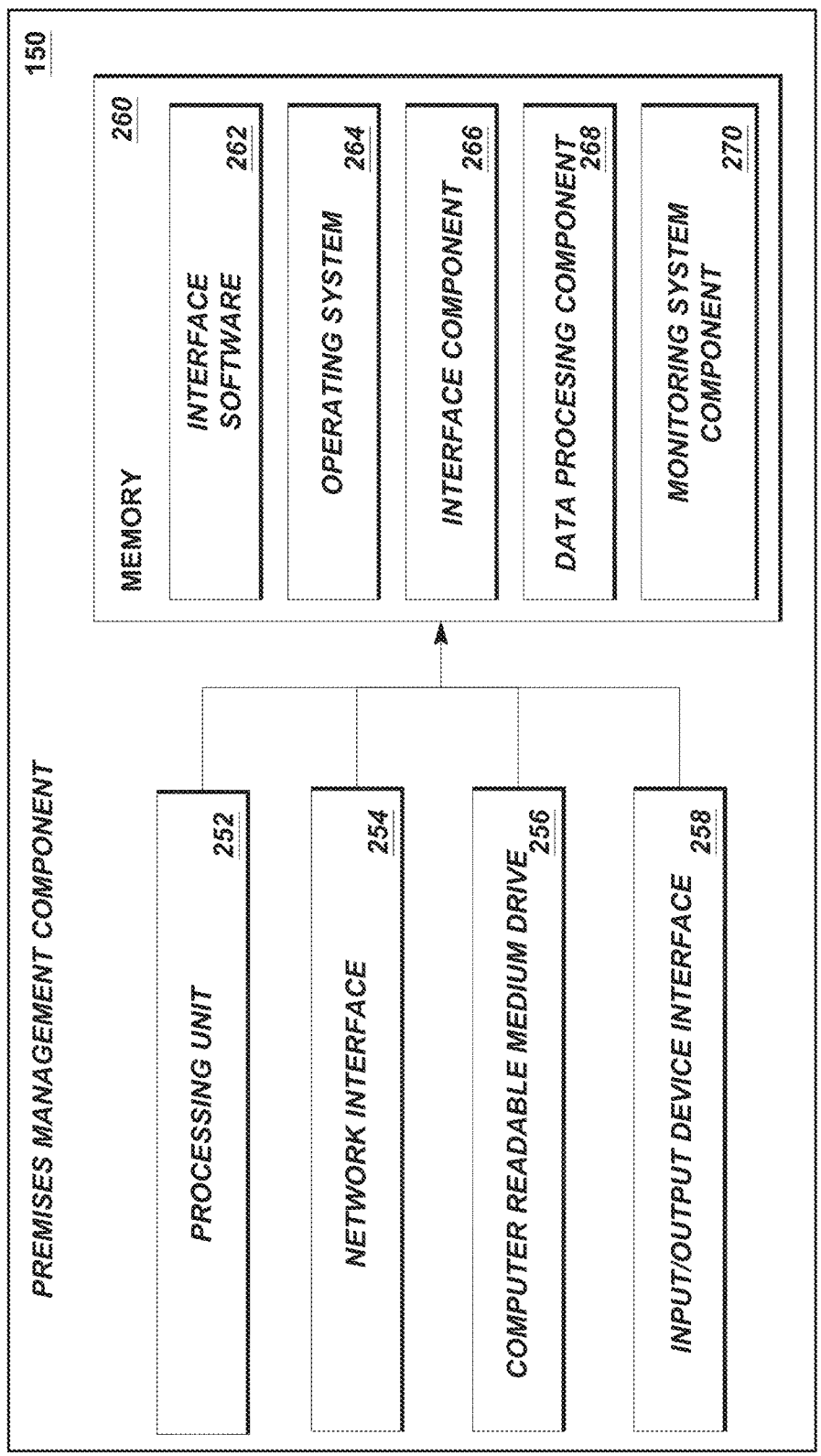
FIG. 2B is a block diagram of illustrative components of a premises management component according to one or more embodiments.

FIG. 2B depicts one embodiment of an architecture of an illustrative premises management component 150. The premises management component 150 can be configured to monitor the premises based on processing data received from one or more appliances and a plurality of sensors associated with the appliances. In some embodiments, each premises management component 150 can be associated with one appliance, multiple appliances, or all of the appliances located in the premises 102. The premises management component 150 can also be configured to generate command instructions based on processing data received from individual's health and behavior profiles received from local device 104, the third-party services 120, and/or machine learning component 114. In some embodiments, the premises management component 150 generates the appliance's operational profile based on data received from the appliances. For example, the one or more appliances transmit the current operational parameters of the appliances, and the operational parameters can be processed as the appliance's operational profile. In some embodiments, the premises management component 150 categorizes the appliance's operational profile based on individual appliances, types of appliances, manufacturers of applications, or other organizational criteria. In other embodiments, the premises management component 150 group the appliances based on appliances located in each premise, which can vary according to different organizational criteria, such as identifiable rooms, individual livable dwellings, groupings of dwellings, individual buildings, the grouping of buildings, and the like.

In some embodiments, the appliance's operational profile can be processed with data received from the plurality of sensors, where each sensor can be associated with one or more appliances. For example, if the appliance is an air filter, and the appliance use sensors (e.g., cooking appliances) that can generate pollutants, the temperature sensor's output data, user movement data, etc., can be associated with the air filter's operational parameters. In this example, if the individual changes the air filter's settings differently, the different settings will be processed with the received or processed sensor data. This data of the appliance's operational parameter associated with the individual's usage or data generated from the plurality of sensors can be referred to as an appliance usage profile. This usage profile can be stored in the internal or external storage medium that communicates with the premises management component 150 using data communication bus. In some embodiments, the usage profile can be stored for each individual or group of individuals, such as a family.

The general architecture of the premises management component 150 depicted in FIG. 2A includes an arrangement of computer hardware and software components that may be used to implement aspects of the present disclosure. As illustrated, the premises management component 150 includes a processing unit 252, a network interface 254, a computer-readable medium drive 256, and an input/output device interface 258, all of which may communicate with one another by way of a communication bus. The components of the premises management component 150 may be physical hardware components or implemented in a virtualized environment.

The network interface 254 may provide connectivity to one or more networks or computing systems, such as the network 106 of FIG. 1. The processing unit 252 may thus receive information and instructions from other computing systems or services via a network. The processing unit 252 may also communicate to and from memory 260 and further provide output information for an optional display via the input/output device interface 258. In some embodiments, the premises management component 150 may include more (or fewer) components than those shown in FIG. 2B.

The memory 260 may include computer program instructions that the processing unit 252 executes in order to implement one or more embodiments. The memory 260 generally includes RAM, ROM, or other persistent or non-transitory memory. The memory 260 may store an operating system 264 that provides computer program instructions for use by the processing unit 252 in the general administration and operation of the premises management component 150. The memory 260 may further include computer program instructions and other information for implementing aspects of the present disclosure. For example, in one embodiment, the memory 260 includes interface software 262 for communicating with other components or services and performing one or more aspects as disclosed herein.

The memory 260 may include an interface component 266 for receiving sensor data generated from the plurality of sensors. In some embodiments, each sensor can be associated with one or more appliances. In some embodiments, the plurality of sensors may transmit the data to the premises processing service via the interface component 266. In these embodiments, the interface component 266 may support a variety of data formats. For example, each of the plurality of sensors may transmit the data in different data formats, and the interface component 266 can be configured to receive or process these different formats. For example, the interface component 266 may convert or parse each of the data received from the plurality of sensors to one or more data formats that can be further used in the premises management component 150. In some embodiments, the interface component 266 receives data from one or more appliances, such as the current operational parameters of the appliance. In these embodiments, each parameter from the operational parameters can have a different data format based on the type of operational parameters or types of appliances. For example, if the appliance is an air conditioner, the data generated from the air conditioner's temperature parameter and power module can have a different data format. In this example, the interface component 266 may convert these appliance operational parameters to one or more data formats utilized in the premises management component 150. In some embodiments, the interface component 266 also receives data from the third-party services 120 or the local devices 104, and these data can be converted into one or more data formats utilized in the premises management component 150.

The memory 260 may also include a data processing component 268 configured to process data received from the appliances and the plurality of sensors. In some embodiments, the data processing component 268 may generate processed data related to the current appliances' operational parameters and data generated from one or more sensors associated with the appliances, and these data can be referred to as the appliance's operational profile. In these embodiments, the data processing component 268 may categorize each appliance's operational profile based on premises, type of appliances, the feature of the appliances, etc. In some embodiments, the data processing component 268 categorizes (e.g., map) the each of the sensor output data based on the appliances corresponding to each sensor. For example, data received from a temperature sensor in a premise can be associated with specific appliances, such as an air conditioner, stove, and humidifier. In these embodiments, the appliance's operational profile associated with one or more data received from the sensors can be stored in internal or external storage mediums. In one embodiment, the appliance's operational profile associated with one or more data received from the sensors can be stored to the database 116 as the usage profile. In some embodiments, the data processing component 268 may identify an individual's health and behavior profiles. For example, a plurality of individuals, where each individual is associated with at least one premise, can have their health and behavior profile generated from the machine learning component 114 or received by the individual via the local device 104. In some embodiments, the data processing component 268 group the individuals based on one or more common premises where the individuals use or reside. For example, a family may use a common premise, and the data processing component 268 may group the individuals in the family.

The memory 260 may also include a monitoring system component 270 for monitoring premises 102. In some embodiments, the monitoring system component 270 may monitor the premises by using the appliance's operational profile and the appliance's usage profile. For example, the monitoring system component 270 may compare the appliance's operational profile and the usage profile. In this example, the appliance's operational profile also includes data generated from the plurality of sensors. In some embodiments, if the appliance's operational profile is different from the usage profile, the monitoring system component 270 may generate a notification to the individual to change one or more appliance's operational profiles. The monitoring system component 270 can also be configured to automatically adjust the appliance's operational parameters based on the data processing result generated from the monitoring system component 270. In some embodiments, the monitoring system component 270 may track one or more operational parameters of at least one appliance. In these embodiments, a data related to the tracking (or monitoring) operational parameter, such as the power consumption of the appliances, can be transmitted remotely to a user and/or third party services. For example, the power consumption of a premise that includes at least one appliance can be transmitted to an electrical power provider via a network in real time or near real time.

Figure 3A:
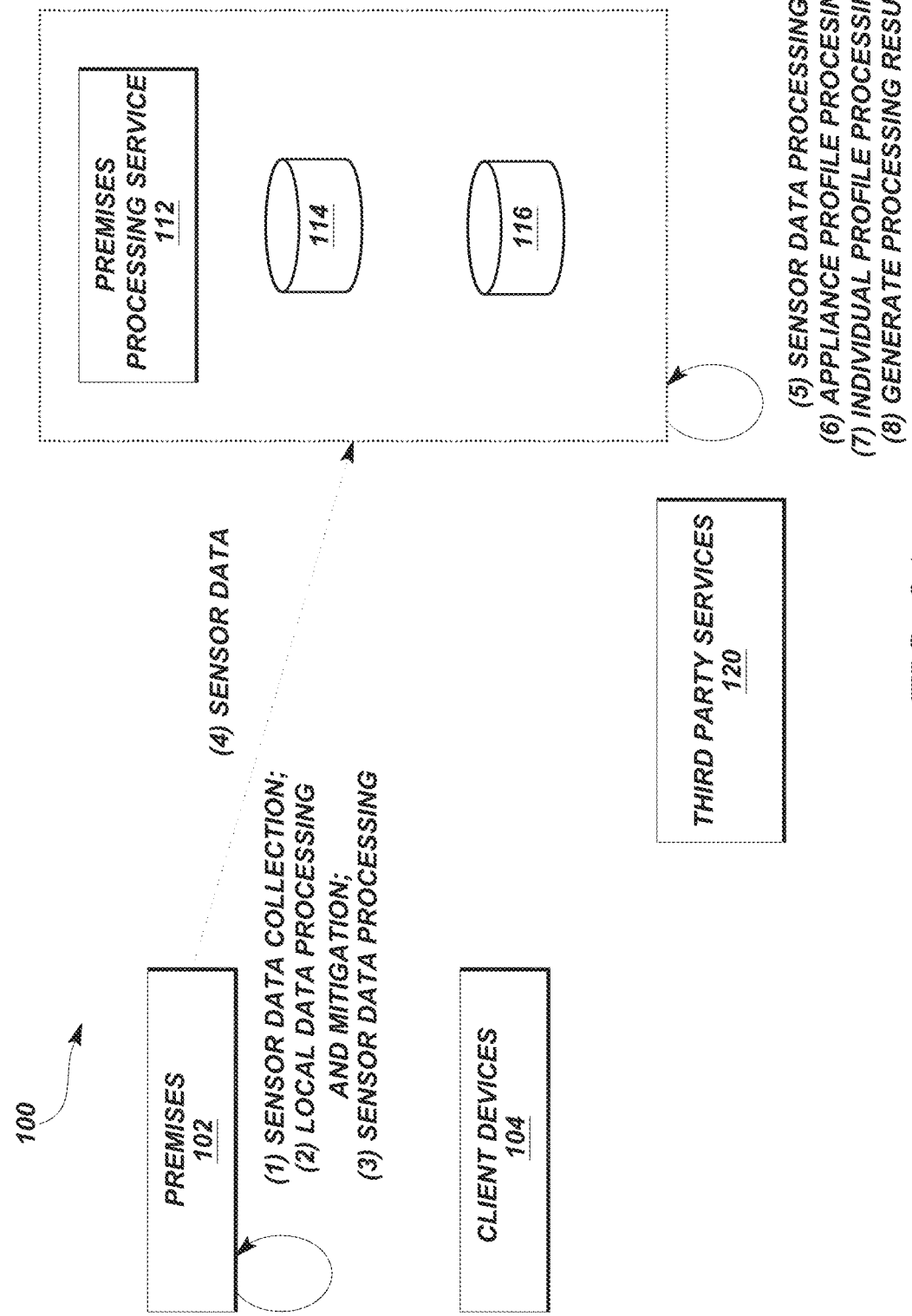
FIG. 3A is an illustrative interaction of generating processing result that can be utilized in one or more embodiments as disclosed herein.
Figure 3B:
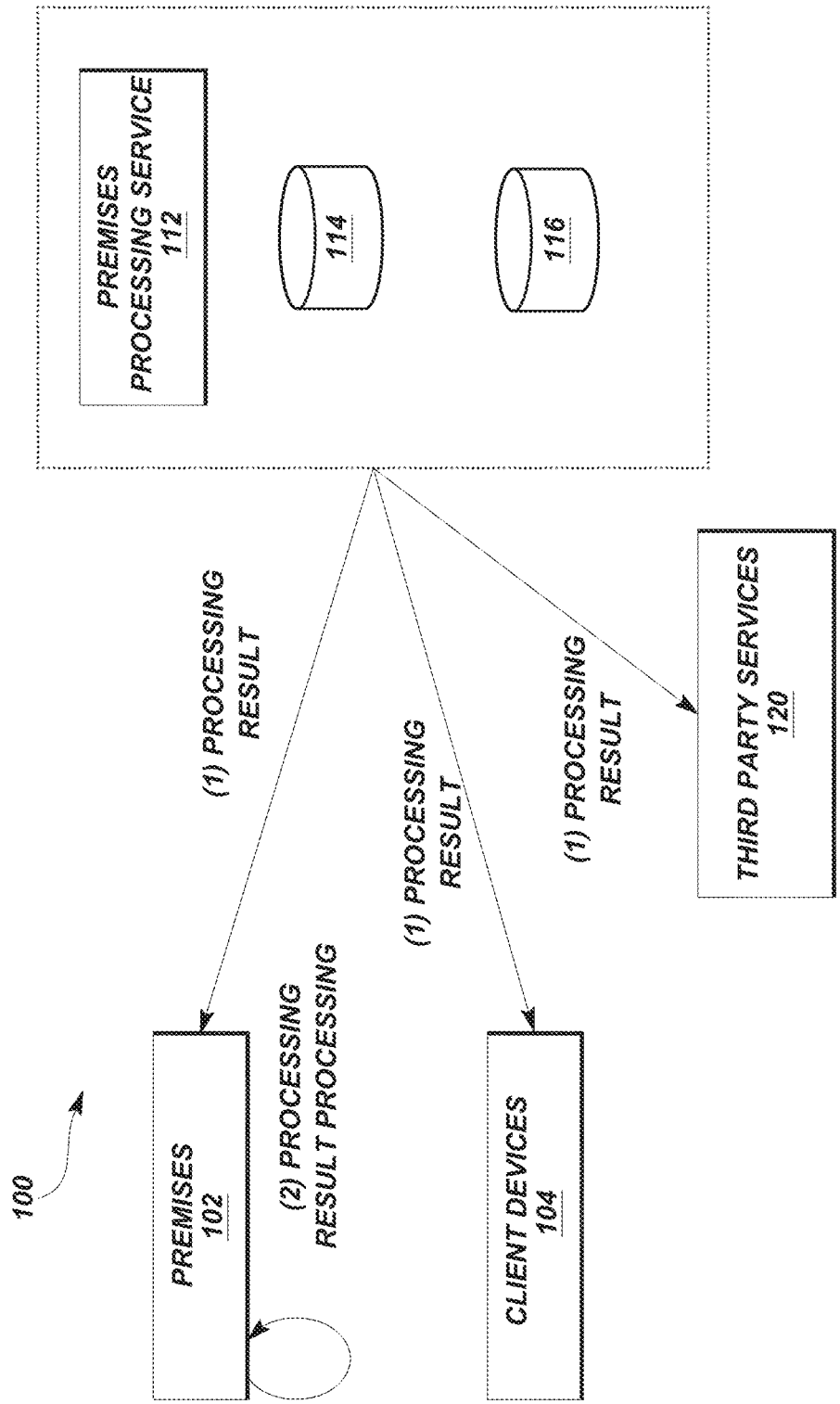
FIG. 3B is an illustrative interaction of performing a processing data received from the premises processing service according to one or more embodiments.

Turning now to FIGS. 3A-3B, illustrative interactions of the components of the system 100, as shown in FIG. 1A, will be described. For purposes of the illustration, it can be assumed that a network provider 110 has been configured in a manner to implement the premises processing service 112. The present application is not intended to be limited to any particular type of service or the number of individual services that may be accessed or generate processing results as part of an execution of an application. Furthermore, the present application is not intended to be limited to the network service provider 110, as depicted in FIG. 1A.

With reference to FIG. 3A, an illustrative interaction of generating processing result that can be utilized in the aspects of premises monitoring and/or generating command instructions, will be described. The interaction is illustrative. At (1), the premises 102 may perform sensor data collection for receiving sensor data generated from the plurality of sensors. In some embodiments, each sensor of the plurality of sensors can be associated with one or more appliances.

At (2), the premises 102 may perform local data processing and mitigation. In some embodiments, the plurality of sensors may transmit the data to the premises 102. In these embodiments, the premises 102 may perform local data processing and mitigation to convert these various data types to data types utilized in the premises 102. For example, each of the plurality of sensors may transmit the data in different data formats, and the premises 102 can be configured to receive or process these different formats. For example, the premises 102 may convert or parse each of the data received from the plurality of sensors to one or more data formats that can be further used in the premises 102. In some embodiments, the premises 102 receives data from one or more appliances, such as the current operational parameters of the appliance. In these embodiments, each parameter from the operational parameters can have different data formats based on the type of operational parameters or types of appliances. For example, if the appliance is an air conditioner, the data generated from the air conditioner's temperature parameter and power module can have a different data format. In this example, the premises 102 may convert these appliance operational parameters to one or more data formats utilized in the premises 102. In some embodiments, the premises 102 also receives data from the third-party services 120 or the local devices 104, and these data can be converted into one or more data formats utilized in the premises 102. For example, the premises 102 may interface with an independent radio signal detection component that can process communication signals (e.g., Wi-Fi network signals) to assess physical movement within a defined area based on determined changes in properties of the communication signals.

At (3), the premises may perform sensor data processing. In some embodiments, the premises 102 may generate processed data related to the current appliances' operational parameters by associating with the sensor data. In these embodiments, the premises 102 may categorize each appliance's operational parameters based on appliances located in a specific premise, type of appliances, the feature of the appliances, etc. In some embodiments, the premises 102 categorize (e.g., map) each of the sensor output data based on the appliances corresponding to each sensor. For example, data received from a temperature sensor in a premise can be associated with specific appliances, such as an air conditioner, stove, and humidifier. In these embodiments, the appliance's operational profile associated with one or more data received from the sensors can be stored as the usage profile.

At (4), the premises 102 may transmit the processed sensor data to the premises processing service 112.

At (5), the premises processing service 112 may perform data processing based on data received from the premises 102. In some embodiments, the premises processing service 112 may generate processed data related to the current appliances' operational parameters by associating with the processed sensor data, and these data can be referred to as the appliance's operational profile. In these embodiments, the premises processing service 112 may categorize each appliance's operational profile based on premises, type of appliances, the feature of the appliances, etc. In some embodiments, the premises processing service 112 categorizes (e.g., map) each of the processed sensor data based on the appliances corresponding to each sensor. For example, data received from a temperature sensor in a premise can be associated with specific appliances, such as an air conditioner, stove, and humidifier. In these embodiments, the appliance's operational profile associated with one or more data received from the sensors can be stored in the database 116 as the usage profile.

At (6), the premises processing service 112 may perform appliance profile processing. In some embodiments, the premises processing service 112 may monitor the premises by using the appliance's operational profile and the appliance's usage profile. For example, the premises processing service 112 may compare the appliance's operational profile and the usage profile. In this example, the appliance's operational profile also includes data generated from the plurality of sensors. In some embodiments, if the appliance's operational profile is different from the usage profile, the premises processing service 112 may generate a notification to the individual to change one or more appliance's operational profiles. The premises processing service 112 can be also configured to automatically adjust the appliance's operational parameters based on the data processing result generated from the premises processing service 112. For example, an appliance's operational profile may require detection of specific individuals (identified by vision systems, audio systems, biometric identification systems, etc.) in order to allow the appliance to be operational.

At (7), the premises processing service 112 may perform individual profile processing. In some embodiments, the premises processing service 112 may identify one or more individual health and behavior profiles. For example, the premises processing service 112 may identify the individual's health and behavior profiles from output data generated from the machine learning component 114. For example, a plurality of individuals, where each individual is associated with at least one premise, can have their health and behavior profile generated from the machine learning component 114. In another example, each individual may provide their profile manually, and the profiles are stored in the database. In some embodiments, the premises processing service 112 groups the individuals based on one or more common premises where the individuals use or reside. For example, a family may use a common premise, and the premises processing service 112 may group the individuals in the family.

In some embodiments, the premises processing service 112 may include one or more appliance usage models based on the individual's health and behavior. For example, the appliances usage model is associated with an agreed, prescribed or selected course of action, such as from a dietitian or physician, that may generally indicate a desired to reduce type of activities related to caloric intake or other types of food consumption behavior. In one aspect, that health and behavior profile indicate that the individual is required to reduce the usage of the microwave during the meal preparation time or that the individual may limit the use of cooking related appliances to certain numbers per day. In this example, the premises processing service 112 may perform the assessment of the individual's usage (e.g., daily usage of the appliances) based on the models, such that if the individual uses microwaves instead of a stove during mealtime or the individual is using the cooking appliances more than the certain times, the premises processing service 112 may provide a notification to the individual. In this regard, the health and behavior profile does not provide a direct correlation to food consumption (e.g., measured or estimated caloric input), but utilizes appliance usage and usage patterns.

In another example, if the individual's behavior indicates that the individual has behavior to save the energy consumption of appliances, the premises processing service 112 may access the operational parameters of the appliances based on motion detection sensors, such that if the air conditioner is set too low temperature, while the detection sensors do not detect the human movement in the premise, the premises processing service 112 may notify to the individual about the power consumption.

At (8), the premises processing service 112 may generate processing results. In some embodiments, the processing results can include a notification to change at least one operational parameter of the appliances. In some embodiments, the processing results can include command instructions to the individual based on the individual processing result at (7).

With reference to FIG. 3B, an illustrative interaction of performing a processing data received from the premises processing service 112. The premises processing service 112 may generate the processing results as described in above, and the processing results can be utilized to modify the appliances' operational parameter. The interaction is illustrative. At (1), the premises processing service 112 may transmit the processing results to the premises 102, client devices 104, and the third party services 120. The processing results are described in FIG. 3A at (8).

At (2), the premises 102 may further process the processing results received from the premises processing service 112. In some embodiments, the premises 102 may automatically process one or more operational parameters of at least one appliance based on the processing results received from the premises processing service 112. In some embodiments, the processing results from the premises processing service 112 can be provided to the local devices 104 in a form of command instructions, and the individual may execute the command instructions by utilizing the local devices 104. Such commands and instructions can also include generating local signals, such as audible commands, visual indicators, audible signals, etc. In some embodiments, the processing results from the premises processing service 112 can be provided to the third party services 120, and the user of the third party services 120 may monitor the premises based on the processing results.

In some embodiments, the premises 102 may identify an individual's health and behavior profiles. For example, the premises-data processing component 218 may identify the individual's health and behavior profiles from output data generated from the machine learning component 114. For example, a plurality of individuals, where each individual is associated with at least one premise, can have their health and behavior profile generated from the machine learning component 114. In another example, each individual may provide their profile manually, and the profiles are stored in the database. In some embodiments, the premises-data processing component 218 group the individuals based on one or more common premises where the individuals use or reside. For example, a family may use a common premise, and the premises-data processing component 218 may group the individuals in the family.

Figure 4:
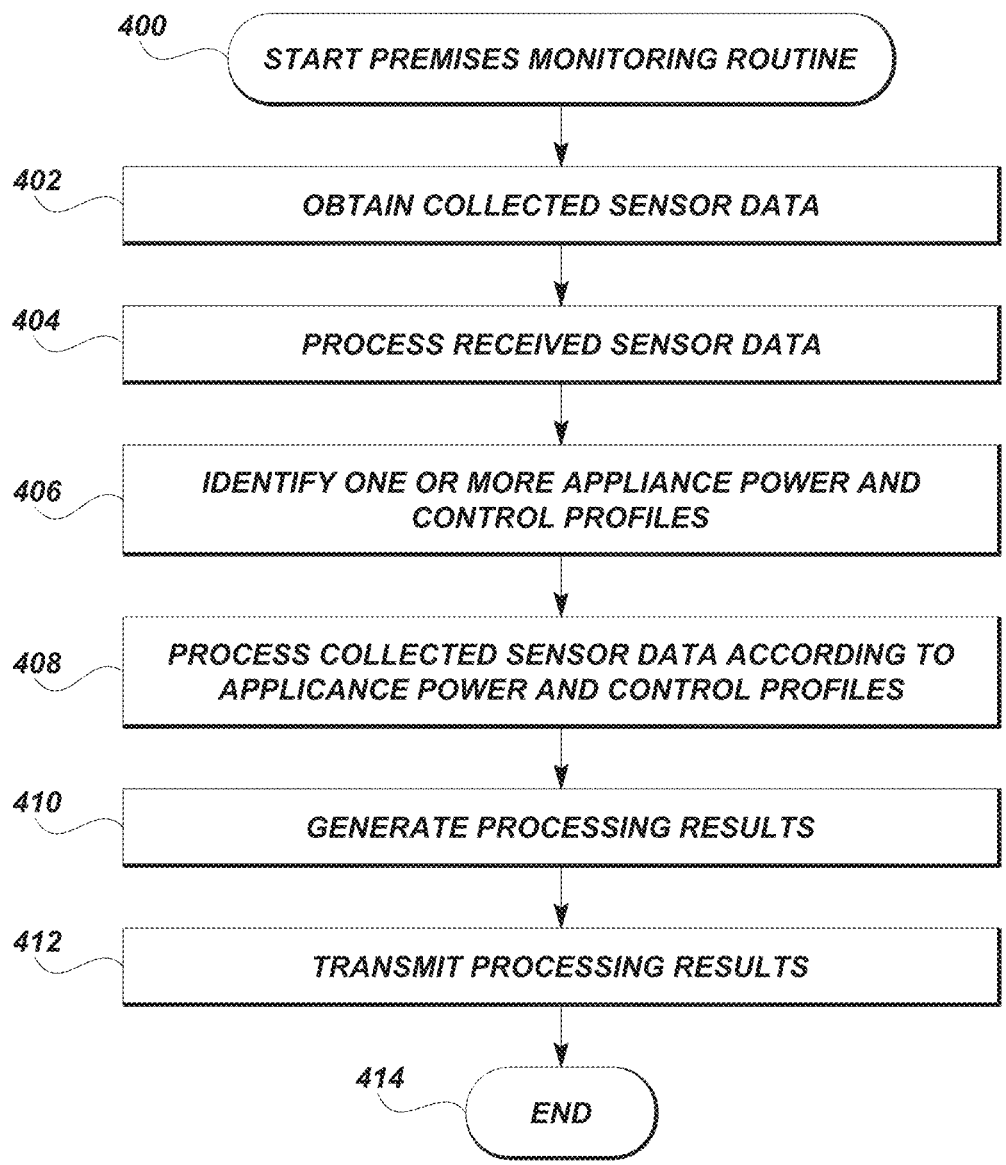
FIG. 4 is a flow diagram illustrative of a routine for premises monitoring routine utilizing the premises.
Figure 5:
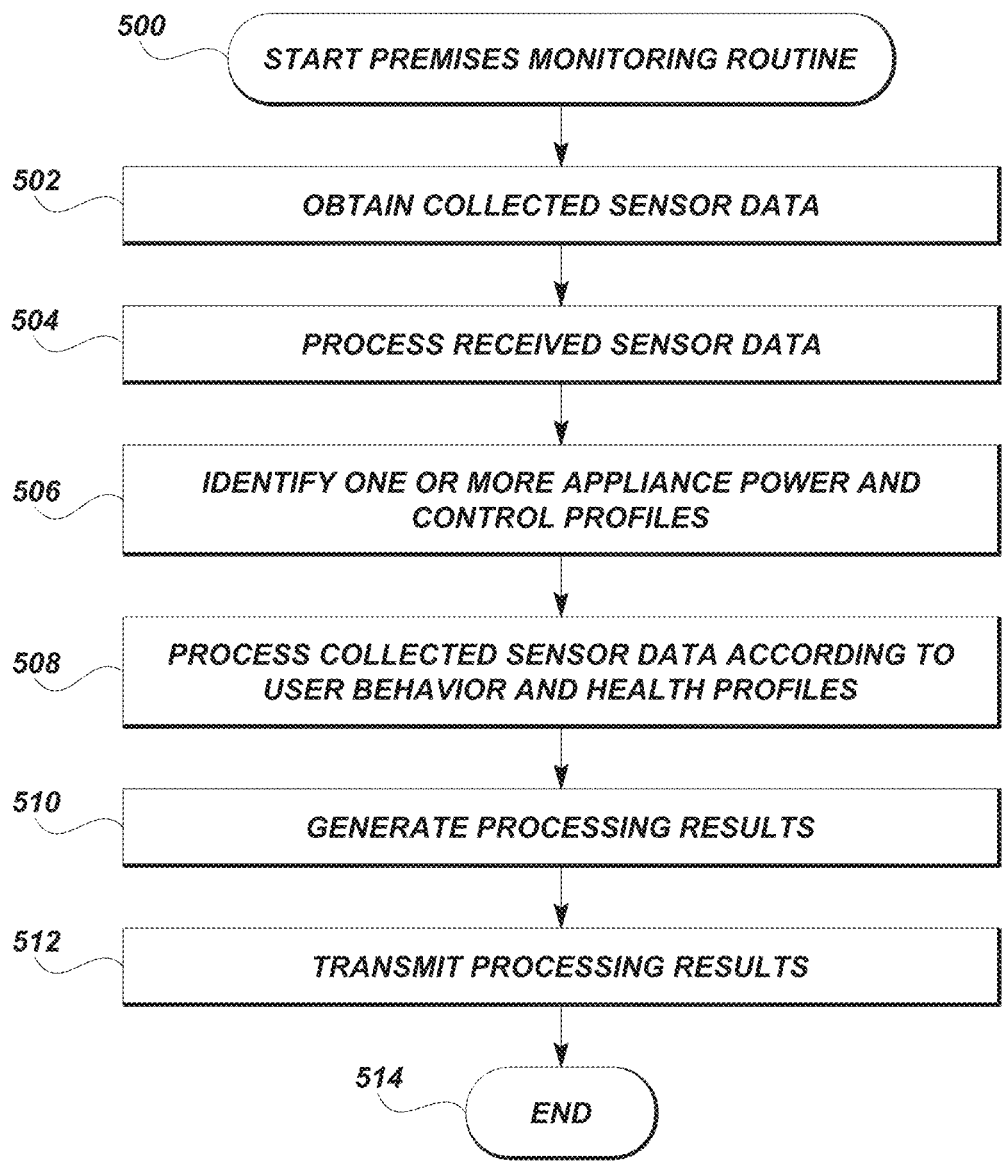
FIG. 5 is a flow diagram illustrative of a routine for premises monitoring routine utilizing the premises processing service.
Figure 6:
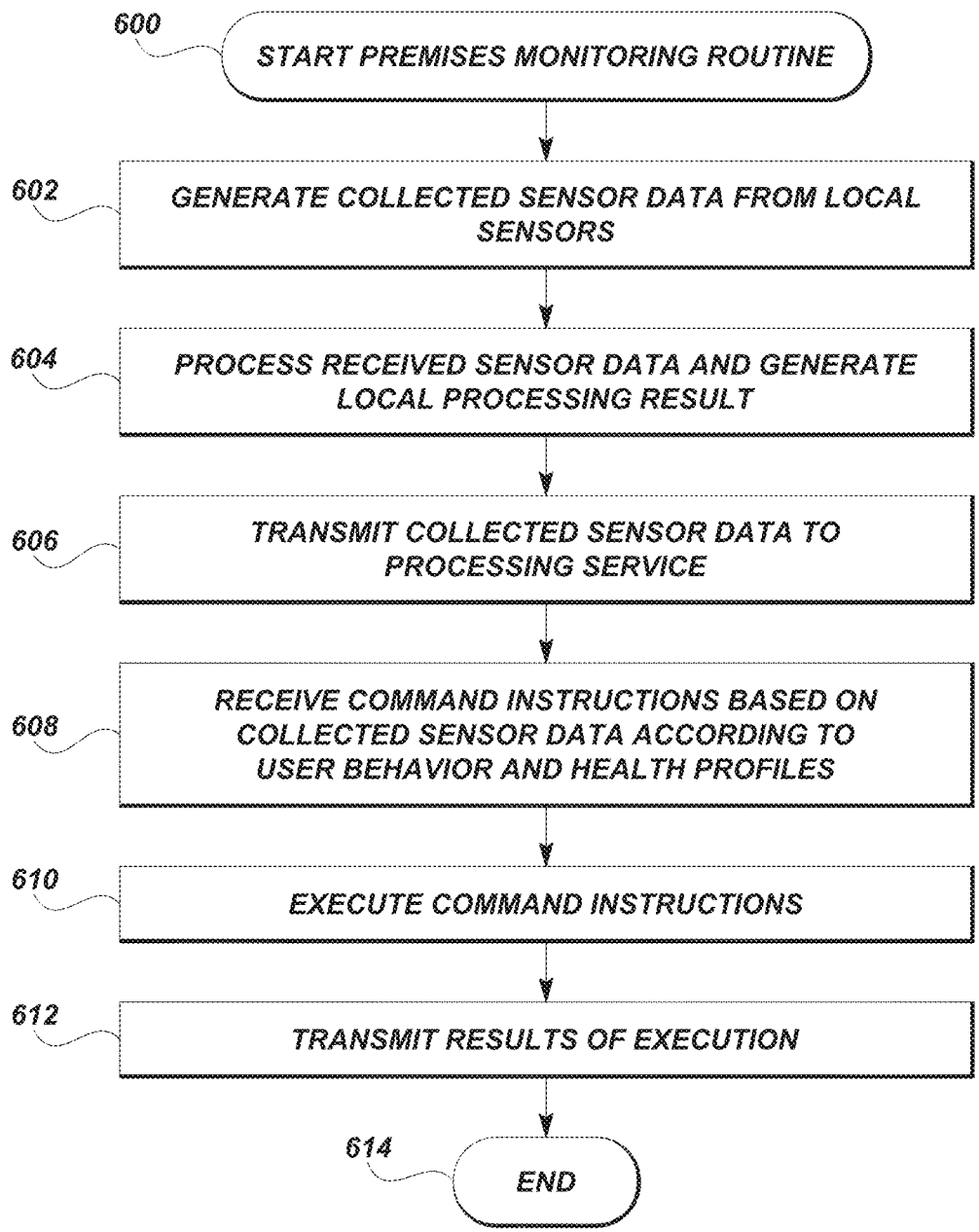
FIG. 6 is a flow diagram illustrative of a routine for premises monitoring routine utilizing the local devices.

Turning now to FIGS. 4-6, a premises monitoring routine based on various aspects, as disclosed in the present disclosure, will be described.

FIG. 4 describes a routine 400 for premises monitoring routine utilizing the premises (e.g., premises management component 150).

At block 402, the premises 102 may obtain sensor data by receiving sensor data generated from the plurality of sensors. In some embodiments, each sensor of the plurality of sensors can be associated with one or more appliances.

At block 404, the premises 102 may process the sensor data received at block 402. In some embodiments, the plurality of sensors may transmit the data to the premises 102. In these embodiments, the premises 102 may perform local data processing and mitigation to convert these various data types to data type utilized in the premises 102. For example, each of the plurality of sensors may transmit the data in different data formats, and the premises 102 can be configured to receive or process these different formats. For example, the premises 102 may convert or parse each of the data received from the plurality of sensors to one or more data formats that can be further used in the premises 102. In some embodiments, the premises 102 receives data from one or more appliances, such as the current operational parameters of the appliance. In these embodiments, each parameter from the operational parameters can have a different data format based on the type of operational parameters or types of appliances. For example, if the appliance is an air conditioner, the data generated from the air conditioner's temperature parameter and power module can have a different data format. In this example, the premises 102 may convert these appliance operational parameters to one or more data formats utilized in the premises 102. In some embodiments, the premises 102 also receives data from the third party services 120 or the local devices 104, and these data can be converted into one or more data formats utilized in the premises 102.

At block 406, the premises 102 may identify one or more appliance's operational profile. In some embodiments, the appliance's current operational parameters can be received by the premises 102 in real time or near real time.

At block 408, the premises 102 may process the collected sensor data according to appliance's operational parameters. In some embodiments, the premises 102 may generate processed data related to the current appliances' operational parameters, such as parameters related to power and control of the appliance, by associating with the sensor data. In these embodiments, the premises 102 may categorize each appliance's operational parameters based on appliances located in a specific premise, type of appliances, the feature of the appliances, etc. In some embodiments, the premises 102 categorize (e.g., map) each of the sensor output data based on the appliances corresponding to each sensor. For example, data received from a temperature sensor in a premise can be associated with specific appliances, such as an air conditioner, stove, and humidifier. In these embodiments, the appliance's operational profile associated with one or more data received from the sensors can be stored as the usage profile.

Further, at block 408, the premises 102 may implement an auto controlling functionality based at least on processing the collected sensor data according to the appliance's operational parameters. In some embodiments, premises 102 can be configured to detect an event that requires immediate control of one or more appliances. Illustratively, if one or more appliances are operating abnormally where the sensors are indicating an immediate control of the appliances, the premises 102 may automatically control the operational parameters of the appliances. For example, if a burner was turned on for a certain duration of time and those sensors, such as proximity sensors, indicating that there is no person around the premises and/or sensors, such as temperature sensors, indicating that the ambient temperature of the premises is above a normal range, the premises 102 may automatically turn off the burner by remotely controlling the operational parameter, such as power controller, of the appliance. As described above, the control of the appliance can include manual controls (e.g., actuating shutoff valves), software instructions, electrical signals, spoken commands, and the like.

At block 410, the premises 102 may generate processing result. In some embodiments, the premises 102 may perform appliance profile processing. In some embodiments, the premises 102 may monitor the premises by using the appliance's operational profile and the appliance's usage profile. For example, the premises 102 may compare the appliance's operational profile and the usage profile. In this example, the appliance's operational profile also includes data generated from the plurality of sensors. In some embodiments, if the appliance's operational profile is different from the usage profile, the premises 102 may generate a notification to the individual to change one or more appliance's operational profile.

At block 412, the premises 102 may transmit the processing result (e.g., processed sensor data) to the premises processing service 112. The premises 102 can also be configured to automatically adjust the appliance's operational parameters based on the data processing result generated from the premises processing service 112.

The routine 400 for premises monitoring routing utilizing the premises 102 can be ended at block 414.

FIG. 5 describes a routine 500 for premises monitoring routine utilizing the premises processing service 112.

At block 502, the premises processing service 112 may obtain sensor data by receiving sensor data generated from the plurality of sensors. In some embodiments, each sensor of the plurality of sensors can be associated with one or more appliances.

At block 504, the premises processing service 112 may process the sensor data received at block 502. In some embodiments, the plurality of sensors may transmit the data to the premises processing service 112 via the network 108. In these embodiments, the premises processing service 112 may perform local data processing and mitigation to convert these various data types to data types utilized in the premises processing service 112. For example, each of the plurality of sensors may transmit the data in different data formats, and the premises processing service 112 can be configured to receive or process these different formats. For example, the premises processing service 112 may convert or parse each of the data received from the plurality of sensors to one or more data formats that can be further used in the premises processing service 112. In some embodiments, the premises processing service 112 receives data from one or more appliances, such as the current operational parameters of the appliance. In these embodiments, each parameter from the operational parameters can have a different data format based on the type of operational parameters or types of appliances. For example, if the appliance is an air conditioner, the data generated from the air conditioner's temperature parameter and power module can have a different data format. In this example, the premises processing service 112 may convert these appliance operational parameters to one or more data formats utilized in the premises processing service 112. In some embodiments, the premises 102 also receives data from the third party services 120 or the local devices 104, and these data can be converted into one or more data formats utilized in the premises 102.

At block 506, the premises processing service 112 may identify one or more appliance's operational profiles. In some embodiments, the appliance's current operational parameters can be received by the premises processing service 112 in real time or near real time.

At block 508, the premises processing service 112 may perform data processing according to individual's health and behavior profiles. In some embodiments, the premises processing service 112 may identify an individual's health and behavior profiles. For example, the premises processing service 112 may identify the individual's health and behavior profiles from output data generated from the machine learning component 114. For example, a plurality of individuals, where each individual is associated with at least one premise, can have their health and behavior profile generated from the machine learning component 114. In another example, each individual may provide their profile manually, and the profiles are stored in the database. In some embodiments, the premises processing service 112 groups the individuals based on one or more common premises where the individuals use or reside. For example, a family may use a common premise, and the premises processing service 112 may group the individuals in the family.

In some embodiments, the premises processing service 112 may include one or more appliance usage models based on the individual's health and behavior. For example, the appliances usage model associated with the individual's body mass index may indicate that the individual is required to reduce the usage of the microwave during the meal preparation time or that the individual may limit the use of cooking related appliances to certain numbers per day. In this example, the premises processing service 112 may perform the assessment of the individual's usage (e.g., daily usage of the appliances) based on the models, such that if the individual uses microwaves instead of a stove during mealtime or that the individual is using the cooking appliances more than the certain times, the premises processing service 112 may provide a notification to the individual. In another example, if the individual's behavior indicates that the individual has behavior to save the energy consumption of appliances, the premises processing service 112 may access the operational parameters of the appliances based on motion detection sensors, such that if the air conditioner is set too low temperature, while the detection sensors do not detect the human movement in the premise, the premises processing service 112 may notify to the individual about the power consumption.

At block 510, the premises processing service 112 may generate processing results. In some embodiments, the processing results can include a notification to change at least one operational parameter of the appliances. In some embodiments, the premises processing service 112 may monitor the premises by using the appliance's operational profile and the appliance's usage profile. For example, the premises processing service 112 may compare the appliance's operational profile and the usage profile. In this example, the appliance's operational profile also includes data generated from the plurality of sensors. In some embodiments, if the appliance's operational profile is different from the usage profile, the premises 102 may generate a notification to the individual to change one or more appliance's operational profiles. In some embodiments, the processing results can include a notification to change at least one operational parameter of the appliances. In some embodiments, the processing results can include command instructions to the individual based on the individual processing result at block 508.

At block 512, the premises processing service 112 may transmit the processing results to the premises 102, client devices 104, and the third party services 120. The routine 500 for premises monitoring routing utilizing the premises 102 can be ended at block 514.

FIG. 6 describes a routine 600 for premises monitoring routine utilizing the local devices 104.

At block 602, the local devices 104 may generate collected sensor data from the plurality of sensors (e.g., local sensors). In some embodiments, each sensor of the plurality of sensors can be associated with one or more appliances.

At block 604, the local devices 104 may process the received sensor data and generate local processing results. In some embodiments, the plurality of sensors may transmit the data to the premises processing service 112 via the network 108. In these embodiments, the premises processing service 112 may perform local data processing and mitigation to convert these various data types to data types utilized in the premises processing service 112. For example, each of the plurality of sensors may transmit the data in different data formats, and the premises processing service 112 can be configured to receive or process these different formats. For example, the premises processing service 112 may convert or parse each of the data received from the plurality of sensors to one or more data formats that can be further used in the premises processing service 112. In some embodiments, the premises processing service 112 receives data from one or more appliances, such as the current operational parameters of the appliance. In these embodiments, each parameter from the operational parameters can have a different data format based on the type of operational parameters or types of appliances. For example, if the appliance is an air conditioner, the data generated from the air conditioner's temperature parameter and power module can have a different data format. In this example, the premises processing service 112 may convert these appliance operational parameters to one or more data formats utilized in the premises processing service 112. In some embodiments, the premises 102 also receives data from the third party services 120 or the local devices 104, and these data can be converted into one or more data formats utilized in the premises 102. In some embodiments, the appliance's current operational parameters can be received by the premises processing service 112 in real time or near real time.

At block 606, the local devices 104 may transmit the collected sensor data to the premises processing service 112. In some embodiments, the premises processing service 112 may identify an individual's health and behavior profiles. For example, the premises processing service 112 may identify the individual's health and behavior profiles from output data generated from the machine learning component 114. For example, a plurality of individuals, where each individual is associated with at least one premise, can have their health and behavior profile generated from the machine learning component 114. In another example, each individual may provide their profile manually, and the profiles are stored in the database. In some embodiments, the premises processing service 112 groups the individuals based on one or more common premises where the individuals use or reside. For example, a family may use a common premise, and the premises processing service 112 may group the individuals in the family.

In some embodiments, the premises processing service 112 may include one or more appliance usage models based on the individual's health and behavior. For example, the appliances usage model associated with the individual's body mass index may indicate that the individual is required to reduce the usage of the microwave during the meal preparation time or that the individual may limit the use of cooking related appliances to certain numbers per day. In this example, the premises processing service 112 may perform the assessment of the individual's usage (e.g., daily usage of the appliances) based on the models, such that if the individual uses microwaves instead of a stove during mealtime or that the individual is using the cooking appliances more than the certain times, the premises processing service 112 may provide a notification to the individual. In another example, if the individual's behavior indicates that the individual has behavior to save the energy consumption of appliances, the premises processing service 112 may access the operational parameters of the appliances based on motion detection sensors, such that if the air conditioner is set too low temperature, while the detection sensors do not detect the human movement in the premise, the premises processing service 112 may notify to the individual about the power consumption.

At block 608, the local devices 104 may receive command instruction based on collected sensor data according to individual's health and behavior profiles. At block 610, the local devices 104 may execute the command instructions. At block 612, the local devices 104 may transmit the result of execution. In some embodiments, the local devices 104 may transmit the processing results to the premises 102, client devices 104, and the third party services 120. The routine 600 for premises monitoring routing utilizing the local devices 104 can be ended at block 614.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be fully automated via software code modules, including one or more specific computer-executable instructions executed by a computing system. The computing system may include one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of customer computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable customer computing device, a device controller, or a computational engine within an appliance, to name a few.

Conditional language such as, among others, "can," "could." "might." or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without customer input or prompting, whether these features, elements and/or steps are included or are to be performed in any particular embodiment.

Disjunctive language such as the phrase "at least one of X, Y, or Z." unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code that include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

What is claimed:

1. A system for managing appliances located in premises, the system comprising:
   one or more computing systems including processing devices and memory, that execute computer-executable instructions, for implementing a premises processing service to:
      obtain, from one or more premises, a plurality of sensor data associated with each of the appliances located in each of the premises, the plurality of sensor data includes at least motion data associated with detected movement of an individual and at least one operational parameters for each of the appliances;
      identify, from the obtained operational parameters for each of the appliances, operational profiles for each of the appliances located in each of the premises, wherein the operational profile includes current operational parameters of each of the appliances;
      identify usage profiles for each of the appliances, wherein the usage profiles include at least historical usage of each of the appliances;
      identify an individual's health and behavior profile, wherein the individual's health and behavior profile is generated from a machine learning component and wherein the machine learning component includes at least one machine learned algorithm to determine the individual's health and behavior profile;
      process, for each of the appliances, the obtained plurality of sensor data based on the identified operational profiles, the individual health and behavior profile, and the usage profiles by comparing the identified operational profiles and the usage profiles with respect to the detected movement of the individual;
      generate one or more instructions to control operational parameters of each of the appliances based on processing results of the identified operational profiles and the usage profiles, and the individual health and behavior profile with respect to the detected movement of the individual; and
      transmit the generated one or more instructions to each of the appliances.

2. The system as recited in claim 1, wherein the at least one operational parameters include power consumption data for each of the appliances.

3. The system as recited in claim 1, wherein the operational profiles include location information for each of the appliances.

4. The system as recited in claim 1, wherein usage profiles include information indicative of historical usage of operational parameters for each of the appliances.

5. The system as recited in claim 4, wherein the appliance usage profiles include historical power consumption information for each of the appliances.

6. The system as recited in claim 1, wherein the generated one or more instructions include at least one of a command or instruction to modify operation of at least one appliance of each of the appliances.

7. The system as recited in claim 1, wherein the premises processing service is further configured to generate usage model for each of the appliances based on the individual's health and behavior profile.

8. The system as recited in claim 7, wherein the premises processing service is further configured to generate a command instruction based on processing results of the usage model and the operational parameters.

9. The system as recited in claim 1, wherein the individual's health and behavior profile includes recommended usage of each of the appliances based on individual's health.

10. A method for managing appliances located in premises, the method comprising:
   obtaining, from one or more premises, a plurality of sensor data associated with one or more appliances located in each of the premises, the plurality of sensor data includes at least motion data associated with presence of an individual within a defined geographic area of the location and at least one operational parameters associated with operation of the one or more appliances;
   identifying an individual's health and behavior profile, wherein the individual's health and behavior profile is generated from a machine learning component, and wherein the machine learning component includes at least one machine learned algorithm to determine the individual's health and behavior profile;

identifying operational profiles for individual appliances in the one or more appliances, wherein the operational profiles include current operational parameters of the individual appliances in the one or more appliances;

identifying usage profiles for individual appliances in the one or more appliances, wherein the usage profiles include at least historical usage of the individual appliances in the one or more appliances;

processing, for the individual appliances in the one or more appliances, the obtained plurality of sensor data based on the identified individual's health and behavior profile, the operational profiles and the usage profiles;

generating a processing result associated with each of the plurality of sensor data; and transmitting the generated processing result.

11. The method as recited in claim 10, wherein the plurality of sensor data includes power consumption data for the individual appliances in the one or more appliances.

12. The method as recited in claim 10, wherein the operational profiles include location information for the individual appliances in the one or more appliances.

13. Method as recited in claim 10, wherein the usage profiles include information indicative of usage of operational parameters of the individual appliances in the one or more appliances.

14. The method as recited in claim 13, wherein the usage profiles include historical power consumption information of the individual appliances in the one or more appliances.

15. The method as recited in claim 10, wherein the generated processing result corresponds to at least one of a command or instruction to modify operation of at least one appliance in the one or more appliances.

16. The method as recited in claim 10, wherein the method further comprising generating a usage model of individual appliances in the one or more appliances based on the individual's health and behavior profile.

17. The method as recited in claim 16, wherein the method further comprising generating a command instruction indicating a recommendation for the individual appliances in the one or more appliances based on a processing result of the operational profile and the usage model.

18. The method as recited in claim 10, wherein the individual's health and behavior profile includes recommended usage of the individual appliances based on individual's health.

19. A system for managing appliances located in premises, the system comprising:

a plurality of local devices, wherein individual local device is configured to:

obtain a plurality of sensor data associated with one or more appliances located in a premises, the plurality of sensor data includes at least motion data associated with detected movement of an individual within a defined geographic area of the location and at least one operational parameters of associated with operation of the one or more appliances;

identify operational profiles of each appliance of the one or more appliances, wherein the operational profiles include current operational parameters of each appliance of the one or more appliances in the premises;

identify usage profiles of each appliance of the one or more appliances, wherein the usage profiles include at least historical usage of each appliance of the one or more appliances;

process, for each appliance of the one or more appliances, the obtained plurality of sensor data based on the identified operational profiles and usage profiles to generate a local processing result;

transmit the local processing result to a premises processing service, wherein the premises processing service generates a command instruction based on the local processing result and an individual's health and behavior profile stored in a database;

receive the command instruction from the premises processing service; and execute the command instruction by receiving an input from an individual user.

20. The system as recited in claim 19, wherein the individual local device is further configured to receive a request to execute the command instruction, wherein the execution of the command instruction is based on the local processing result and the individual's health and behavior profile; and wherein the execution includes controlling operational parameters of at least one appliance of the one or more appliances.

21. The system as recited in claim 19, wherein the plurality of sensor data includes power consumption data for each appliance of the one or more appliances.

22. The system as recited in claim 19, wherein the local processing result includes operational parameters of each appliance of the one or more appliances and data generated from the sensors, the data associated with at least one of the operational parameters of each appliance of the one or more appliances.

23. The system as recited in claim 19, wherein the local processing result further includes the usage profiles, and wherein the usage profiles includes information indicative of historical operational usage of each appliance of the one or more appliances.

24. The system as recited in claim 23, wherein the appliance usage profiles include historical power consumption information for each appliance of the one or more appliances.

25. The system as recited in claim 19, wherein the individual's health and behavior profile is generated from a machine learning component, wherein the machine learning component includes at least one machine learned algorithm to determine the individual's health and behavior profile.

26. The system as recited in claim 19, wherein the premises processing service further configured to generate usage model of each appliance of the one or more appliances based on the individual's health and behavior profile.

27. The system as recited in claim 26, wherein the premises processing service further configured to generate a command instruction based on processing result of the operational profiles and the usage model.

28. The system as recited in claim 19, wherein the individual's health and behavior profile includes recommended usage of each appliance of one or more appliances based on individual's health.

* * * * *